US008865939B2

(12) United States Patent
Yoshimura et al.

(10) Patent No.: US 8,865,939 B2
(45) Date of Patent: Oct. 21, 2014

(54) METHOD FOR PRODUCING TRANS-1,4-BIS(AMINOMETHYL) CYCLOHEXANE

(75) Inventors: Naritoshi Yoshimura, Funabashi (JP); Shinji Kiyono, Kimitsu (JP); Tetsuya Hamada, Ichihara (JP); Eiji Watanabe, Chiba (JP); Saiko Sawada, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 13/878,090

(22) PCT Filed: Oct. 5, 2011

(86) PCT No.: PCT/JP2011/073005
§ 371 (c)(1),
(2), (4) Date: Apr. 5, 2013

(87) PCT Pub. No.: WO2012/046782
PCT Pub. Date: Apr. 12, 2012

(65) Prior Publication Data

US 2013/0197270 A1 Aug. 1, 2013

(30) Foreign Application Priority Data

Oct. 7, 2010 (JP) ................................ 2010-227744

(51) Int. Cl.

| | |
|---|---|
| ***C07C 209/00*** | (2006.01) |
| ***C07C 253/34*** | (2006.01) |
| ***C07C 209/48*** | (2006.01) |
| ***C07C 253/22*** | (2006.01) |
| *B01J 23/44* | (2006.01) |
| *B01J 25/00* | (2006.01) |
| *B01J 25/02* | (2006.01) |

(52) U.S. Cl.

CPC ........... *C07C 209/48* (2013.01); *C07B 2200/09* (2013.01); *B01J 23/44* (2013.01); *B01J 25/00* (2013.01); *B01J 25/02* (2013.01); *C07C 253/34* (2013.01); *C07C 2101/14* (2013.01); *C07C 253/22* (2013.01)

USPC ............ 564/451; 564/448; 564/449; 564/450

(58) Field of Classification Search

CPC ........................... C07C 209/48; C07C 209/72
USPC ................................. 564/448, 449, 450, 451
See application file for complete search history.

(56) References Cited

U.S. PATENT DOCUMENTS

| | | | |
|---|---|---|---|
| 3,377,374 | A | 4/1968 | Hale, Jr. et al. |
| 5,969,187 | A | 10/1999 | Okawa et al. |
| 2005/0014973 | A1 | 1/2005 | Endou et al. |
| 2008/0051600 | A1 | 2/2008 | Endou et al. |
| 2013/0197269 | A1 | 8/2013 | Yoshimura et al. |

FOREIGN PATENT DOCUMENTS

| | | | | |
|---|---|---|---|---|
| CN | 1229322 | C | | 11/2005 |
| CN | 1915958 | A | | 2/2007 |
| CN | 101591237 | A | | 12/2009 |
| EP | 1 219 586 | A2 | | 7/2002 |
| JP | 41-021338 | B | | 12/1966 |
| JP | 60-224665 | A | | 11/1985 |
| JP | 63-010752 | A | | 1/1988 |
| JP | 63-255252 | A | | 10/1988 |
| JP | 07-030006 | B2 | | 4/1995 |
| JP | 10-259167 | A | | 9/1998 |
| JP | 10-306066 | A | | 11/1998 |
| JP | 10-330329 | A | | 12/1998 |
| JP | 11-335335 | A | | 12/1999 |
| JP | 2001-181223 | | | 7/2001 |
| JP | 2001-187765 | A | | 7/2001 |
| JP | 2003-026638 | | | 1/2003 |
| JP | 2008-143832 | A | | 6/2008 |
| JP | 2010-163439 | A | | 7/2010 |
| JP | 2011-006382 | A | | 1/2011 |
| JP | 2011006382 | A | * | 1/2011 |
| WO | WO-00/78701 | A1 | | 12/2000 |
| WO | WO-2012/046781 | A1 | | 4/2012 |

OTHER PUBLICATIONS

International Search Report PCT/JP2011/073005 dated Dec. 27, 2011.
R. Malachowski et al., Berichte Der Deutschen Chemischen Gesellschaft, vol. 71, No. 4, pp. 759-767, 1938.
International Preliminary Report on Patentability PCT/JP2011/073005 dated Apr. 9, 2013.
Written Opinion of the International Searching Authority PCT/JP2011/073005 dated May 8, 2013.
Chinese Office Action issued on Dec. 3, 2013 in Chinese Application No. 201180048400.4 (corresponding to the present US app).

* cited by examiner

*Primary Examiner* — Sudhakar Katakam
(74) *Attorney, Agent, or Firm* — Foley & Lardner LLP

(57) ABSTRACT

A method for producing trans-1,4-bis(aminomethyl)cyclohexane includes a nuclear hydrogenation step of producing a hydrogenated terephthalic acid or terephthalic acid derivative by nuclear hydrogenation of a terephthalic acid or terephthalic acid derivative, the terephthalic acid or terephthalic acid derivative being at least one selected from the group consisting of terephthalic acid, terephthalic acid ester, and terephthalic acid amide; a cyanation step of treating the hydrogenated terephthalic acid or terephthalic acid derivative with ammonia, thereby producing 1,4-dicyanocyclohexane, and producing trans-1,4-dicyanocyclohexane from the obtained 1,4-dicyanocyclohexane; and an aminomethylation step of treating the trans-1,4-dicyanocyclohexane with hydrogen, thereby producing trans-1,4-bis(aminomethyl)cyclohexane. Metal oxide is used as a catalyst in the cyanation step, and the obtained trans-1,4-dicyanocyclohexane has a metal content of 3000 ppm or less.

17 Claims, No Drawings

METHOD FOR PRODUCING TRANS-1,4-BIS(AMINOMETHYL) CYCLOHEXANE

CROSS-REFERENCE TO RELATED APPLICATIONS

This application is a national phase application of PCT/JP2011/073005, filed Oct. 5, 2011, which claims priority to Japanese application 2010-227744, filed Oct. 7, 2010.

TECHNICAL FIELD

The present invention relates to a method for producing trans-1,4-bis(aminomethyl)cyclohexane.

BACKGROUND ART

Heretofore, 1,4-bis(aminomethyl)cyclohexane has been well known for a raw material of polyamide used for fiber, film, etc. Also, 1,4-bis(isocyanatomethyl)cyclohexane derived from 1,4-bis(aminomethyl)cyclohexane is useful as a raw material of polyurethane used for, for example, paints, adhesives, plastic lenses, etc.

Such 1,4-bis(aminomethyl)cyclohexane includes two types of stereo isomers, i.e., trans-1,4-bis(aminomethyl)cyclohexane (hereinafter may be referred to as trans isomer) and cis-1,4-bis(aminomethyl)cyclohexane (hereinafter may be referred to as cis isomer), and it has been known that the ratio of the cis isomer to the trans isomer in 1,4-bis(aminomethyl) cyclohexane affects various physical properties of polyamide or polyurethane produced by using the 1,4-bis(aminomethyl) cyclohexane.

For example, in the case of polyamide, the higher the ratio of the trans isomer in the raw material 1,4-bis(aminomethyl) cyclohexane is, the better the physical properties of melting point or thermal stability are, allowing production of polyamide suitable for fiber, film, etc.

In the case of polyurethane, by using, as a raw material, 1,4-bis(isocyanatomethyl)cyclohexane derived from 1,4-bis (aminomethyl)cyclohexane having a high ratio of trans isomer, polyurethane with excellent heat resistance and solubility in a solvent can be obtained.

Thus, in various industrial fields, a method for producing 1,4-bis(aminomethyl)cyclohexane having a high ratio of trans isomer has been desired.

As methods for producing 1,4-bis(aminomethyl)cyclohexane having a high ratio of trans isomer, for example, the following has been known: performing nuclear hydrogenation (addition of hydrogen to aromatic rings) of p-xylylenediamine in the presence of a ruthenium catalyst or a rhodium catalyst to produce 1,4-bis(aminomethyl)cyclohexane containing the cis isomer and the trans isomer; heating the 1,4-bis(aminomethyl)cyclohexane containing the cis isomer and the trans isomer in the presence of a platinum group catalyst to isomerize the cis isomer to the trans isomer; and thereafter, separating and recovering the 1,4-bis(aminomethyl)cyclohexane having a high trans isomer ratio from the isomerized solution, for example, by distillation (Patent Document 1) or by crystallization (Patent Document 2).

For a method for producing p-xylylenediamine used in the above-described method, for example, Patent Document 3 has proposed ammoxidation of p-xylene using a metal oxide catalyst such as vanadium to produce terephthalonitrile, and hydrogenating the terephthalonitrile in the presence of a nickel catalyst.

Furthermore, as a method for producing trans-1,4-bis(aminomethyl)cyclohexane, for example, Non-Patent Document 1 (Malachowski et al.) discloses the following: trans-1,4-cyclohexanedicarboxylic acid is allowed to react with thionyl chloride and followed by the reaction with ammonia to produce trans-1,4-cyclohexanedicarboxamide via acid chloride; and the trans-1,4-cyclohexanedicarboxamide is further allowed to react with thionyl chloride to obtain trans-1,4-dicyanocyclohexane, and then the obtained trans-1,4-dicyanocyclohexane is hydrogenated to produce trans-1,4-bis (aminomethyl)cyclohexane.

CITATION LIST

Patent Document

Patent Document 1
Japanese Unexamined Patent Publication No. H11-335335
Patent Document 2
Japanese Unexamined Patent Publication No. H10-306066
Patent Document 3
Japanese Unexamined Patent Publication No. 2003-26638

Non-Patent Document

Non-Patent Document 1
Berichte Der Deutschen Chemischen Gesellschaft, vol. 71, No. 4, p 759 (1938)

SUMMARY OF THE INVENTION

Problem to be Solved by the Invention

However, when p-xylylenediamine is produced as a raw material of trans-1,4-bis(aminomethyl)cyclohexane by the method described in Patent Document 3, p-xylene has to be subjected to ammoxidation at a very high temperature of 420° C. to produce terephthalonitrile, and thereafter, the obtained terephthalonitrile has to be hydrogenated under a very high pressure of 12 MPa (Patent Document 3 (ref: Example 1)).

Furthermore, when 1,4-bis(aminomethyl)cyclohexane is produced by the method described in Patent Document 1 or 2 from the thus obtained p-xylylenediamine, nuclear hydrogenation of p-xylylenediamine under a very high pressure of 100 kg/cm$^2$ (10 MPa) has to be performed (ref: Patent Document 1 and 2 (Reference Examples)).

That is, in the methods described in Patent Documents 1 to 3, the components have to be reacted at a high temperature and under a high pressure, and therefore improvements in terms of equipment and safety are desired.

Furthermore, with the methods described in Patent Document 1 or 2, isomerization of the obtained cis-1,4-bis(aminomethyl)cyclohexane to the trans isomer requires use of an expensive catalyst of the platinum group, and moreover, the trans isomer ratio after the reaction is 80% or less, and therefore to improve the trans isomer ratio, further separation steps, for example, distillation and crystallization are necessary (ref: Patent Documents 1 and 2 (CLAIMS)).

Thus, the methods described in Patent Documents 1 to 2 involve high production costs, and therefore improvements in terms of economy are desired.

Also, the method described in Non-Patent Document 1 includes steps of multiple stages, and furthermore, requires use of a large amount of thionyl chloride, which is highly corrosive and thus hard to handle, and on top of that, the reaction yield in each of the steps is low.

Thus, in the method described in Non-Patent Document 1, in view of industrial production, improvements in terms of many aspects are desired.

The present invention was achieved in view of those disadvantages, and its object is to provide a method that is excellent in terms of equipment, safety, and economy for producing trans-1,4-bis(aminomethyl)cyclohexane.

Means for Solving the Problem

To achieve the above object, a method for producing trans-1,4-bis(aminomethyl)cyclohexane of the present invention includes:

a nuclear hydrogenation step of producing a hydrogenated terephthalic acid or terephthalic acid derivative by nuclear hydrogenation of a terephthalic acid or terephthalic acid derivative, the terephthalic acid or terephthalic acid derivative being at least one selected from the group consisting of terephthalic acid, terephthalic acid ester, and terephthalic acid amide;

a cyanation step of treating the hydrogenated terephthalic acid or terephthalic acid derivative obtained in the nuclear hydrogenation step with ammonia to produce 1,4-dicyanocyclohexane, and producing trans-1,4-dicyanocyclohexane from the obtained 1,4-dicyanocyclohexane; and an aminomethylation step of treating the trans-1,4-dicyanocyclohexane obtained in the cyanation step with hydrogen, thereby producing trans-1,4-bis(aminomethyl)cyclohexane, wherein metal oxide is used as a catalyst in the cyanation step, and the obtained trans-1,4-dicyanocyclohexane has a metal content of 3000 ppm or less.

A method for producing trans-1,4-bis(aminomethyl)cyclohexane of the present invention includes:

a cyanation step of treating a hydrogenated terephthalic acid or terephthalic acid derivative with ammonia, thereby producing 1,4-dicyanocyclohexane, and producing trans-1,4-dicyanocyclohexane from the obtained 1,4-dicyanocyclohexane; and an aminomethylation step of treating the trans-1,4-dicyanocyclohexane obtained in the cyanation step with hydrogen, thereby producing trans-1,4-bis(aminomethyl)cyclohexane, wherein metal oxide is used as a catalyst in the cyanation step, and the obtained trans-1,4-dicyanocyclohexane has a metal content of 3000 ppm or less.

In the above-described production method, it is preferable that the hydrogenated terephthalic acid or terephthalic acid derivative is obtained by a nuclear hydrogenation step of nuclear hydrogenation of a terephthalic acid or terephthalic acid derivative, the terephthalic acid or terephthalic acid derivative being at least one selected from the group consisting of terephthalic acid, terephthalic acid ester, and terephthalic acid amide.

In the method for producing trans-1,4-bis(aminomethyl)cyclohexane of the present invention, it is preferable that in the cyanation step, the cis isomer and the trans isomer in the 1,4-dicyanocyclohexane obtained from the reaction with ammonia are separated, and the separated trans-1,4-dicyanocyclohexane is used in the aminomethylation step.

In the method for producing trans-1,4-bis(aminomethyl)cyclohexane of the present invention, it is preferable that in the cyanation step, trans-1,4-dicyanocyclohexane is separated from 1,4-dicyanocyclohexane by crystallization using an aqueous solvent, and in the crystallization step of the cyanation step and in the aminomethylation step, the same aqueous solvent is used.

In the method for producing trans-1,4-bis(aminomethyl)cyclohexane of the present invention, it is preferable that in the cyanation step, the separated cis-1,4-dicyanocyclohexane is brought into contact again with ammonia in the presence of or in the absence of the hydrogenated terephthalic acid or terephthalic acid derivative.

In the method for producing trans-1,4-bis(aminomethyl)cyclohexane of the present invention, it is preferable that in the cyanation step, the reaction with ammonia is performed at the temperature from 200 to 350° C.

In the method for producing trans-1,4-bis(aminomethyl)cyclohexane of the present invention, it is preferable that in the cyanation step, the reaction with ammonia is performed in the presence of a solvent having a boiling point of 180° C. to 350° C.

In the method for producing trans-1,4-bis(aminomethyl)cyclohexane of the present invention, it is preferable that in the cyanation step, the contact with ammonia is performed in the presence of 3 to 20 parts by weight of a solvent relative to 100 parts by weight of the hydrogenated terephthalic acid or terephthalic acid derivative.

In the method for producing trans-1,4-bis(aminomethyl)cyclohexane of the present invention, it is preferable that a solvent is used in the cyanation step, the solvent being selected from o-dichlorobenzene, triethylene glycol dimethylether, tetraethylene glycol dimethylether, N-methyl-2-pyrrolidinone, N,N'-dimethylimidazolidinone, N,N'-diethylimidazolidinone, N,N'-dipropylimidazolidinone, N,N',4-trimethylimidazolidinone, and N,N'-dimethylpropyleneurea.

In the method for producing trans-1,4-bis(aminomethyl)cyclohexane of the present invention, it is preferable that in the cyanation step, the ammonia to be brought into contact with is fed at a rate greater than 0.5 mol equivalent/hydrogenated terephthalic acid or terephthalic acid derivative/hr.

Effects of the Invention

The method for producing trans-1,4-bis(aminomethyl)cyclohexane of the present invention is excellent in terms of equipment, safety, and economy, and achieves safe, low costs, and high yield production of trans-1,4-bis(aminomethyl)cyclohexane. Thus, the present invention can be suitably used as an industrial method for producing trans-1,4-bis(aminomethyl)cyclohexane.

EMBODIMENT OF THE INVENTION

A method for producing trans-1,4-bis(aminomethyl)cyclohexane of the present invention includes a nuclear hydrogenation step of producing a hydrogenated terephthalic acid or terephthalic acid derivative by nuclear hydrogenation of a terephthalic acid or terephthalic acid derivative, the terephthalic acid or terephthalic acid derivative being at least one selected from the group consisting of terephthalic acid, terephthalic acid ester, and terephthalic acid amide;

a cyanation step of treating the hydrogenated terephthalic acid or terephthalic acid derivative obtained in the nuclear hydrogenation step with ammonia to produce 1,4-dicyanocyclohexane, and producing trans-1,4-dicyanocyclohexane from the obtained 1,4-dicyanocyclohexane; and an aminomethylation step of treating the trans-1,4-dicyanocyclohexane obtained in the cyanation step with hydrogen, thereby producing trans-1,4-bis(aminomethyl)cyclohexane. Each step is described in detail in the following.

[Nuclear Hydrogenation Step]

In the nuclear hydrogenation step, nuclear hydrogenation of a terephthalic acid or terephthalic acid derivative is performed, the terephthalic acid or terephthalic acid derivative being at least one selected from the group consisting of terephthalic acid, terephthalic acid ester, and terephthalic acid amide, to produce a corresponding hydrogenated terephthalic acid or terephthalic acid derivative (that is, hydrogenated terephthalic acid or terephthalic acid derivative of at least one selected from the group consisting of cyclohexane-1,4-dicarboxylic acid, cyclohexane-1,4-dicarboxylic acid ester, and cyclohexane-1,4-dicarboxylic acid amide).

In the nuclear hydrogenation step, for example, the method described in Japanese Unexamined Patent Publication No. 2001-181223 may be used.

The terephthalic acid or terephthalic acid derivative used as a raw material in the present invention may be one having quality of industrially available products, and also undried (containing water) terephthalic acid or terephthalic acid derivative that has undergone the purification in the hydrogenation step generally performed in production of terephthalic acid may be used.

The reaction in the nuclear hydrogenation step is exothermic reaction, and therefore to suitably suppress the temperature increase due to the heat of reaction, and also to increase conversion, it is preferable that a solvent that is inactive in such a reaction is added as a diluent to the raw material terephthalic acid or terephthalic acid derivative so that the terephthalic acid or terephthalic acid derivative concentration in the reaction solution is, for example, 1 to 50 wt %, preferably 2 to 30 wt %. When the concentration in the reaction solution is within the range, it is advantageous in that the reaction rate is not reduced, and the temperature increase in the reactor is small.

Examples of such a solvent include aqueous solvents such as water, methanol, ethanol, 1-propanol, isopropanol, 1-butanol, 2-butanol, t-butanol, and 1,4-dioxane.

Use of such an aqueous solvent is advantageous in that the reaction mixture in the nuclear hydrogenation step can be cooled as necessary, and re-circulated for use.

In this case, water is used preferably because it can be recovered by separation operation thereafter; it does not allow unwanted components to be mixed into the reaction system; and undried terephthalic acid that underwent the purification step of terephthalic acid can be used.

In the nuclear hydrogenation step, hydrogen used in the nuclear hydrogenation may be of industrial use quality. For example, the hydrogen may contain inactive gas (e.g., nitrogen, methane, etc.) but its hydrogen concentration is preferably 50% or more.

The hydrogen amount is preferably about 3 to 50 times the raw material terephthalic acid or terephthalic acid derivative in molar ratio.

When the hydrogen amount is within such a range, the amount of unreacted materials is small, the reaction rate is sufficient, and it is advantageous economically.

In the nuclear hydrogenation step, a known catalyst may be added.

The catalyst used in the nuclear hydrogenation step is a general noble metal catalyst for nuclear hydrogenation. To be specific, examples of such a catalyst include palladium, platinum, ruthenium, and rhodium, and preferably, palladium or ruthenium is used.

These catalysts are preferably prepared as a supported catalyst. Examples of carriers for such catalysts include activated carbon, alumina, silica, and kieselguhr, and preferably, activated carbon or silica is used.

The amount of metal (e.g., palladium, platinum, ruthenium, rhodium, etc.) supported is in the range of, for example, 0.1 to 10 wt %, preferably 0.5 to 10 wt %, of the total amount including the catalyst carrier.

When the amount of metal supported is within such a range, it is preferable because the activity of catalyst per weight is high.

The catalyst is used in the form of, for example, powder, granular, or may be supported on a pellet carrier. Preferably, the catalyst is in the form of powder. When the catalyst has an appropriate size, for example, when the catalyst is powder catalyst, the catalyst contains an internal portion that effectively contributes to reaction in a large amount, and therefore the reaction rate does not easily decrease.

The catalyst amount relative to 100 parts by weight of terephthalic acid or terephthalic acid derivative is in the range of, for example, 0.1 to 50 parts by weight, preferably 0.5 to 20 parts by weight.

The terephthalic acid or terephthalic acid derivative is not highly soluble in general solvents such as water, and therefore the reaction is preferably performed in a suspension of the raw material and the solvent.

The reactor is preferably a pressure-resistant vessel.

A raw material slurry and hydrogen are introduced from the reactor top or bottom, and brought into contact with the catalyst in a suspension. After the reaction, the product, i.e., hydrogenated terephthalic acid or terephthalic acid derivative, is highly soluble in a general solvent such as water at high temperature, and therefore separation from the catalyst can be performed by filtration.

In the filtration, the above-described product is dissolved in, for example, a known alkaline solution (e.g., aqueous sodium hydroxide solution, etc.), and after the solution is filtered, the solution can be neutralized by a known acid solution (e.g., aqueous hydrogen chloride solution, etc.).

Thereafter, by drying or concentrating the mixture, or by crystallizing the product by cooling, hydrogenated terephthalic acid or terephthalic acid derivative can be obtained.

The reaction temperature is usually in the range of 50 to 200° C., and preferably 100 to 160° C.

The reaction temperature within such a range is advantageous in that the amount of unreacted materials and by-products is less, hydrogenolysis does not occur easily, and as a result, the yield increases.

The reaction pressure is usually in the range of 0.5 to 15 MPa, preferably 2 to 15 MPa, more preferably 2 to 8 MPa, even more preferably 2 to 5 MPa.

The reaction pressure within such a range is advantageous in that the reaction rate does not easily decrease, and the amount of by-products is less.

The conversion of terephthalic acid or terephthalic acid derivative is usually 90% or more, preferably 95% or more, and more preferably 98% or more.

When the amount of the unreacted terephthalic acid or terephthalic acid derivative is small as described above, it is advantageous in that after treatment such as separation and purification of the product from the reaction mixture become not so complicated.

The hydrogenated terephthalic acid or terephthalic acid derivative obtained in the nuclear hydrogenation step is a mixture of a cis isomer (that is, cis-cyclohexane-1,4-dicarboxylic acid, cis-cyclohexane-1,4-dicarboxylic acid ester, and/or cis-cyclohexane-1,4-dicarboxylic acid amide) and a trans isomer (that is, trans-cyclohexane-1,4-dicarboxylic acid, trans-cyclohexane-1,4-dicarboxylic acid ester, and/or trans-cyclohexane-1,4-dicarboxylic acid amide).

[Cyanation Step]

In the cyanation step, the above-described hydrogenated terephthalic acid or terephthalic acid derivative obtained in the nuclear hydrogenation step is treated with ammonia to produce 1,4-dicyanocyclohexane, and the trans and cis isomers are separated from the produced 1,4-dicyanocyclohexane to obtain trans-1,4-dicyanocyclohexane.

In the cyanation step, for example, the method described in Japanese Unexamined Patent Publication No. S63-10752 may be used.

To be more specific, in the cyanation step, the hydrogenated terephthalic acid or terephthalic acid derivative obtained in the nuclear hydrogenation step is allowed to react with a compound capable of serving as an ammonia source (e.g., ammonia, urea, ammonium carbonate, etc.) (hereinafter may be referred to as an ammonia source) by heating at, usually 200° C. or more and below 350° C., preferably 230° C. or more and below 320° C.

The reaction temperature within such a range is advantageous in that the reaction rate does not decrease, and decomposition due to excessive heating occurs less.

In the present invention, metal oxide is used as a catalyst in the cyanation step.

Examples of metal oxide include silica, alumina, phosphorus pentoxide, tin oxide, titanium oxide, zinc oxide, iron oxide, zirconium oxide, and cobalt oxide.

Of these metal oxides, in view of easy separation after reaction, silica, alumina, tin oxide, titanium oxide, zinc oxide, iron oxide, zirconium oxide, or cobalt oxide is preferably used.

In this step, furthermore, metal oxide and other catalysts can be used in combination, and examples of such a catalyst include mineral acids such as hydrochloric acid, phosphoric acid, and sulfuric acid, and organic acids such as acetic acid, propionic acid, and benzoic acid.

When metal oxide and other catalyst are used in combination, the mixing ratio of these is not particularly limited, and is set suitably in accordance with the purpose and application.

The catalyst is used in the form of, for example, powder, granular, or may be supported on a pellet carrier. Preferably, the catalyst is powder.

When the catalyst has a suitable size, for example, when the catalyst is powder, the internal portion in the catalyst that effectively contributes to reaction is large, and reaction rate does not easily decrease.

The amount of catalyst relative to 100 parts by weight of hydrogenated terephthalic acid or terephthalic acid derivative is in the range of, for example, 0.1 to 50 parts by weight, preferably 0.5 to 20 parts by weight.

In the reaction, a solvent is preferably used as appropriate.

Examples of the solvent include, although any solvent that does not inhibit the purpose of the method of the present invention can be used, aliphatic or alicyclic hydrocarbons such as decane, undecane, dodecane, tridecane, tetradecane, pentadecane, and decalin; aromatic hydrocarbons such as mesitylene, tetralin, butylbenzene, p-cymene, diethylbenzene, diisopropylbenzene, triethylbenzene, cyclohexylbenzene, dipentylbenzene, and dodecylbenzene; alcohols such as hexanol, 2-ethylhexanol, octanol, decanol, dodecanol, ethylene glycol, diethylene glycol, and triethylene glycol; ethers such as diethylene glycol dimethylether, triethylene glycol dimethyl ether, tetraethylene glycol dimethylether, o-dimethoxybenzene, ethylphenylether, butylphenylether, and o-diethoxybenzene; halogenated aromatic hydrocarbons such as iodobenzene, o-dichlorobenzene, m-dichlorobenzene, 1,2,4-trichlorobenzene, o-dibromobenzene, bromochlorobenzene, o-chlorotoluene, p-chlorotoluene, p-chloroethylbenzene, and 1-chloronaphthalene; polar aprotic solvents such as dimethyl sulfoxide, N,N-dimethylformamide, N,N-dimethylacetamide, hexamethylphosphoramide, N-methyl-2-pyrrolidinone, N,N'-dimethylimidazolidinone, N,N'-diethylimidazolidinone, N,N'-dipropylimidazolidinone, N,N',4-trimethylimidazolidinone, and N,N'-dimethylpropyleneurea; and the product in this step, i.e., 1,4-dicyanocyclohexane. These solvents may be used singly or in a combination of two or more.

As the solvent, in view of suppressing crystallization of 1,4-dicyanocyclohexane to the gas purge line of the reactor, and to apparatuses at downstream of the reactor such as a condenser, the solvent is preferably selected from, for example, ethers such as diethylene glycol dimethylether, triethylene glycol dimethylether, tetraethylene glycol dimethylether, o-dimethoxybenzene, ethylphenylether, butylphenylether, and o-diethoxybenzene; halogenated aromatic hydrocarbons such as iodobenzene, o-dichlorobenzene, m-dichlorobenzene, 1,2,4-trichlorobenzene, o-dibromobenzene, bromochlorobenzene, o-chlorotoluene, p-chlorotoluene, p-chloroethylbenzene, and 1-chloronaphthalene; and polar aprotic solvents such as dimethyl sulfoxide, N,N-dimethylformamide, N,N-dimethylacetamide, hexamethylphosphoramide, N-methyl-2-pyrrolidinone, N,N'-dimethylimidazolidinone, N,N'-diethylimidazolidinone, N,N'-dipropylimidazolidinone, N,N',4-trimethylimidazolidinone, and N,N'-dimethylpropyleneurea.

Of the above-described solvents, those solvents having a boiling point of 180° C. to 350° C. is preferably used. Use of the solvent having a boiling point lower than 180° C. is not preferable because the energy load on the reactor increases. Use of the solvent having a boiling point higher than 350° C. is not preferable because the effects of suppressing the crystallization of 1,4-dicyanocyclohexane to the reactor gas purge line and to apparatuses at downstream of the reactor such as a condenser decreases.

In view of the above, of the above-described solvents, selection is made preferably from o-dichlorobenzene, triethylene glycol dimethylether, tetraethylene glycol dimethylether, N-methyl-2-pyrrolidinone, N,N'-dimethylimidazolidinone, N,N'-diethylimidazolidinone, N,N'-dipropylimidazolidinone, N,N',4-trimethylimidazolidinone, and N,N'-dimethylpropyleneurea.

The amount of solvent used is not particularly limited, and usually is 10 times or less by weight the reactant (including the above-described hydrogenated terephthalic acid or terephthalic acid derivative obtained in the nuclear hydrogenation step), preferably 1 time or less by weight the reactant, and more preferably 3 to 20 parts by weight relative to 100 parts by weight of the hydrogenated terephthalic acid or terephthalic acid derivative. When the amount of the solvent is small, or when no solvent is used, suppression of crystallization of 1,4-dicyanocyclohexane to the gas purge line of the reactor and to apparatuses at downstream of the reactor such as a condenser becomes difficult, and when the amount of the solvent is large, it is not preferable because energy load on the reactor increases.

The reaction method is not particularly limited, and examples thereof include slurry-bed batch process, semi-batch process, and continuous process; and also fixed-bed continuous process. Preferably, liquid-phase slurry reaction is used.

The reactor is preferably a pressure-resistant vessel.

For example, a hydrogenated terephthalic acid or terephthalic acid derivative, and a catalyst are introduced from the reactor top or bottom, and the hydrogenated terephthalic acid or terephthalic acid derivative is dissolved by heating to be suspended; and an ammonia supply source compound such as ammonia is fed intermittently or continuously to the reactor, to allow reaction at a predetermined temperature.

The amount of the ammonia supply source compound to be fed is, in view of making ammonia easy to treat and recover after reaction, for example, 1 to 20 mol, preferably 2 to 20 mol relative to 1 mol of hydrogenated terephthalic acid or terephthalic acid derivative.

The rate of the feeding of the ammonia source is not particularly limited, and preferably 0.1 mol to 2 mol relative to 1 mol of hydrogenated terephthalic acid or terephthalic acid derivative per 1 hour, and more preferably, more than 0.5 mol and 2 mol or less (that is, more than 0.5 mol equivalent/hydrogenated terephthalic acid or terephthalic acid derivative/hr and 2 mol equivalent/hydrogenated terephthalic acid or terephthalic acid derivative/hr or less).

The feeding rate lower than 0.5 mol relative to 1 mol of hydrogenated terephthalic acid or terephthalic acid derivative per 1 hour is not preferable because the reaction requires a long time. The feeding rate higher than 2 mol relative to 1 mol of hydrogenated terephthalic acid or terephthalic acid derivative per 1 hour is disadvantageous economically in that the unreacted ammonia source increase in volume, and therefore, for example, when ammonia is to be recovered and reused, the burden is substantial.

The feeding time is suitably selected depending on the feeding rate. For example, the feeding time is 1 to 80 hours, preferably 2 to 50 hours.

Water is produced as a by-product in this reaction, and therefore in view of accelerating the reaction, water is preferably removed out of the system. To remove water out of the system, for example, an inactive gas such as nitrogen can be fed to the reactor.

The reaction may be performed under any pressure condition, for example, under elevated pressure, ambient pressure, and reduced pressure, which is suitably selected.

After the reaction, the product, i.e., 1,4-dicyanocyclohexane, is obtained as a mixture (stereoisomers) of cis-1,4-dicyanocyclohexane (cis isomer) and trans-1,4-dicyanocyclohexane (trans isomer).

The cis isomer/trans isomer ratio of the 1,4-dicyanocyclohexane obtained converges to the equilibrium composition ratio of 1,4-dicyanocyclohexane at the reaction temperature, approximately, to cis isomer/trans isomer=40/60 to 60/40, regardless of the stereo isomer ratio of the hydrogenated terephthalic acid or terephthalic acid derivative.

From the mixture of the cis- and trans-1,4-dicyanocyclohexane after reaction, the catalyst used is removed by a known method, for example, such as filtration and adsorption, and thereafter, trans-1,4-dicyanocyclohexane is separated therefrom, for example, by fractional crystallization using the difference in their solubility, or by distillation using the difference in their boiling points. Of these methods, simple and easy fractional crystallization is preferable.

Separation of the trans isomer and the cis isomer from the mixture of cis- and trans-1,4-dicyanocyclohexane is preferable for excellent operability and separation efficiency to the separation of the trans isomer (trans-1,4-bis(aminomethyl) cyclohexane) and the cis isomer (cis-1,4-bis(aminomethyl) cyclohexane) from the mixture of cis- and trans-1,4-bis(aminomethyl)cyclohexane, for example.

The solvent used in the fractional crystallization is preferably a solvent in which the solubility of the cis isomer and its of the trans isomer of 1,4-dicyanocyclohexane is greatly different, and examples thereof include water; lower fatty acids such as acetic acid; alcohols such as methanol, ethanol, 1-propanol, isopropanol, 1-butanol, 2-butanol, t-butanol, and ethylene glycol; and ethers such as diethylether and 1,4-dioxane.

The above-described solvent is preferably the same as the solvent used in the aminomethylation step to be described later, particularly because it does not necessitates the drying step of the product, and specifically, selected from aqueous solvents such as water and alcohols.

In the fractional crystallization, first, 1,4-dicyanocyclohexane is dissolved in the above-described solvent, and the mixture is heated. Thereafter, the mixture is cooled to ambient temperature. This allows 1,4-dicyanocyclohexane having a high proportion of trans isomer to be crystallized (crystallization step). Thereafter, the crystallized 1,4-dicyanocyclohexane can be separated by filtration.

After the separation, as necessary, the mixture is washed and dried so that trans-1,4-dicyanocyclohexane in solid state can be obtained. The thus obtained trans-1,4-dicyanocyclohexane is preferably used in the aminomethylation step to be described later.

The purity (trans isomer ratio) of trans-1,4-dicyanocyclohexane can be suitably controlled by the conditions in fractional crystallization. The purity (trans isomer ratio) of trans-1,4-dicyanocyclohexane is approximately 85% or more, preferably 90% or more.

When metal oxide is used as a catalyst in the above-described cyanation reaction, a metal component of the catalyst used may be contaminated in the obtained trans-1,4-dicyanocyclohexane as an impurity. The metal content is 3000 ppm or less, preferably 2000 ppm or less, and more preferably, 1500 ppm or less relative to trans-1,4-dicyanocyclohexane.

More than 3000 ppm metal contents are not preferable because resulting metal might inhibit the reaction in the aminomethylation step to be described later.

As necessary, the metal content is preferably reduced by various methods, for example, by a method in which catalyst removal operation such as filtration and adsorption after reaction are repeated; a method in which the solution of 1,4-dicyanocyclohexane before crystallization is brought into contact with activated carbon, synthetic adsorbent, etc. and then separated by filtration, and thereafter crystallized; and a method in which the trans-1,4-dicyanocyclohexane having a large amount of metal contents is re-dissolved in the above-described solvent, then brought into contact with activated carbon, synthetic adsorbent, etc. then separated by filtration, and thereafter, the solvent is distilled off.

Meanwhile, in the filtrate after the filtration, the 1,4-dicyanocyclohexane having a high cis isomer ratio is dissolved.

The 1,4-dicyanocyclohexane having a high cis isomer ratio obtained by distilling off the solvent from the filtrate is again fed into the reactor in the cyanation step, to be treated again with ammonia in the presence of or in the absence of hydrogenated terephthalic acid or terephthalic acid derivative.

In this manner, thermal isomerization occurs at a predetermined temperature in the reactor of the cyanation step to form an equilibrium composition mixture of cis isomer/trans isomer, therefore this is advantageous in that trans-1,4-dicyanocyclohexane can be obtained with a small loss.

When 1,4-dicyanocyclohexane having a high cis isomer ratio is fed again in the absence of hydrogenated terephthalic acid or terephthalic acid derivative to the reactor of the cyanation step, only the isomerization reaction is performed at a predetermined temperature. At that time, the presence of metal oxide and/or ammonia is not necessary, but in view of shortening the reaction time, ammonia is preferably present.

The amount of ammonia to be present is sufficient when the amount allows the ammonia concentration of the reaction solution in the reactor to be saturated continuously, and the amount of ammonia source to be fed is, in view of making ammonia easy to treat or recover after the reaction, for example, 0.1 to 10 mol, preferably 0.1 to 5 mol relative to 1 mol of 1,4-dicyanocyclohexane.

The rate of the ammonia source to be fed is not particularly limited, and in view of feeding the amount that allows for the ammonia concentration in the reaction solution in the reactor is saturated during the reaction continuously as described above, the rate is 0.01 mol to 1 mol relative to 1 mol of 1,4-dicyanocyclohexane per 1 hour.

[Aminomethylation Step]

In the aminomethylation step, the trans-1,4-dicyanocyclohexane obtained in the cyanation step is treated with hydrogen, thereby producing trans-1,4-bis(aminomethyl)cyclohexane.

In the aminomethylation step, for example, the method described in, for example, Japanese Unexamined Patent Publication No. 2001-187765 can be used.

An industrial use hydrogen is sufficient in terms of quality as the hydrogen used in the aminomethylation step, and the hydrogen may contain inactive gas (e.g., nitrogen, methane, etc.). The hydrogen concentration is preferably 50% or more.

As the hydrogenation catalyst used in the aminomethylation step, a known hydrogenation catalyst, for example, any of a cobalt catalyst, a nickel catalyst, a copper catalyst, and a noble metal catalyst can be used.

In view of reactivity and selectivity, a catalyst mainly composed of nickel, cobalt and/or ruthenium is preferably used, and more preferably, Raney catalyst or a catalyst supported on porous metal oxides such as silica, alumina, silica alumina, kieselguhr, and activated carbon is preferably used.

The catalyst may further contain metals such as aluminum, zinc, and silicon.

These hydrogenation catalysts may contain, as a reaction accelerator, a metal selected from chromium, iron, cobalt, manganese, tungsten, and molybdenum.

The hydrogenation catalyst can be used as a perfect solid catalyst, or can be used as a supported solid catalyst, for example, nickel, cobalt, or ruthenium supported on aluminum oxide, titanium oxide, zirconium oxide, magnesia/alumina, etc.

The catalyst is in the form of, for example, powder, granular, or may be supported on a pellet carrier may be used. Preferably, the catalyst is powder. When the catalyst has an appropriate size, for example, when the catalyst is powder catalyst, the catalyst contains an internal portion that effectively contributes to reaction in a large amount, and therefore the reaction rate does not easily decrease.

The amount of catalyst used is, in view of reactivity and selectivity, for example, 0.1 to 20 parts by weight, preferably 0.5 to 15 parts by weight relative to 100 parts by weight of trans-1,4-dicyanocyclohexane.

For the reaction, a solvent can be used suitably, and examples of such a solvent include aqueous solvents such as water; alcohols such as methanol, ethanol, 1-propanol, isopropanol, 1-butanol, 2-butanol, and t-butanol; and 1,4-dioxane.

For the solvent, preferably, those solvents used in the fractional crystallization in the above-described cyanation step can be used.

The trans-1,4-dicyanocyclohexane concentration in the reaction solution is, for example, 1 to 50 wt %, preferably 2 to 40 wt %.

The trans-1,4-dicyanocyclohexane concentration in the reaction solution within such a range is advantageous in that the reaction rate does not decrease, and the temperature increase in the reactor is small.

The reaction is preferably performed in the presence of ammonia.

The ammonia works to suppress production of by-products such as secondary amine, tertiary amine, and polyamine, i.e., products other than the target trans-1,4-bis(aminomethyl)cyclohexane, that is, works to improve reaction selectivity.

The amount of ammonia used is, in view of suppressing production of the above-described by-products, preventing decrease in the hydrogenation rate, and making ammonia easy to treat or recover after reaction, for example, 0.05 to 5 mol, preferably 0.1 to 2.5 mol relative to 1 mol of trans-1,4-dicyanocyclohexane.

The reaction method is not particularly limited, and examples thereof include a slurry-bed batch process, a semi-batch process, a continuous process, and a fixed-bed continuous process. Preferably, liquid-phase slurry reaction is used.

The reactor is preferably a pressure-resistant vessel.

For example, trans-1,4-dicyanocyclohexane, catalyst, hydrogen, and as necessary a solvent and ammonia are introduced from the reactor top or bottom, and the mixture is allowed to react at a predetermined temperature.

The reaction pressure is usually 0.1 to 20 MPa, preferably 0.5 to 10 MPa, more preferably 0.5 to 8 MPa, and particularly preferably 0.5 to SMPa.

The reaction temperature is, in view of reactivity and selectivity, for example, 50 to 250° C., preferably 50 to 200° C., more preferably 70 to 150° C., and preferably, the reaction temperature is increased during the hydrogenation reaction continuously or stepwise.

After the reaction, trans-1,4-bis(aminomethyl)cyclohexane can be separated from the reaction mixture by a known method, for example, by filtration, distillation, etc.

The purity (trans isomer ratio) of trans-1,4-bis(aminomethyl)cyclohexane can be suitably controlled by the conditions of the reaction and the separation. The purity (trans isomer ratio) of trans-1,4-bis(aminomethyl)cyclohexane is approximately 80% or more, preferably 85% or more.

The method for producing trans-1,4-bis(aminomethyl)cyclohexane of the present invention is excellent in terms of equipment, safety, and economy, and achieves safe, low costs, and high yield production of trans-1,4-bis(aminomethyl)cyclohexane.

Thus, the method can be suitably used as an industrial method for producing trans-1,4-bis(aminomethyl)cyclohexane.

The above-described method for producing trans-1,4-bis(aminomethyl)cyclohexane includes the nuclear hydrogenation step, the cyanation step, and the aminomethylation step. However, in the method for producing trans-1,4-bis(aminomethyl)cyclohexane, for example, hydrogenated terephthalic acid or terephthalic acid derivative is used as a starting material to omit the nuclear hydrogenation step, and the cyanation step and the aminomethylation step can be performed.

In such a case, the hydrogenated terephthalic acid or terephthalic acid derivative as a starting material is not limited to the above-described hydrogenated terephthalic acid or terephthalic acid derivative obtained in the nuclear hydrogenation step. However, with the above-described nuclear hydrogenation step, hydrogenated terephthalic acid or terephthalic acid derivative can be obtained safely at low costs and with high yields, and therefore the hydrogenated terephthalic acid or terephthalic acid derivative as a starting material is preferably obtained by the above-described nuclear hydrogenation step.

EXAMPLES

Hereinafter, the present invention will be described more specifically with reference to Examples. However, the present invention is not limited to those Examples. Analysis in the nuclear hydrogenation step was performed by high-performance liquid chromatography, and analyses in the cyanation step and the aminomethylation step were performed by gas chromatography. The metal component amount was analyzed by ICP (inductively coupled plasma) emission spectroscopy.

Example 1

Nuclear Hydrogenation Step

A 100 mL stainless steel-made autoclave equipped with a stirrer was charged with 25.0 g of terephthalic acid, 2.8 g of a catalyst (10% Pd/C, manufactured by NE Chemcat Corporation), and 100 mL of water. The autoclave was purged with nitrogen introduced from the autoclave nozzle inlet three times at 5 MPa, and the mixture was heated to 150° C. while stirring at 400 rpm.

When the temperature reached 150° C., hydrogen supply was started intermittently to achieve a pressure of 3.5 MPa, and the reaction was performed until there is no hydrogen absorption.

After the completion of reaction, the product was cooled to room temperature. The reaction mixture was taken out, and after a 5N aqueous NaOH solution containing sodium hydroxide of 2.5 times mol the charged terephthalic acid amount was added thereto, the mixture was filtered to remove the catalyst.

The filtrate was neutralized with a 5N aqueous HCl solution, and then analyzed by high-performance liquid chromatography. It was found that the conversion rate of terephthalic acid was 100%, the yield of 1,4-cyclohexanedicarboxylic acid was 99%, and the trans isomer/cis isomer ratio was 33/67.

[Cyanation Step]

A four-neck flask equipped with a stirrer, a gas inlet tube, a thermometer, a gas purge line, and a condenser was charged with 9.3 g of 1,4-cyclohexanedicarboxylic acid obtained by concentrating the filtered reaction solution obtained in the nuclear hydrogenation step and 0.13 g of tin (II) oxide, and the mixture was heated to 170° C. while stirring at 300 rpm, thereby dissolving carboxylic acid.

Thereafter, ammonia gas was introduced at a rate of 16 mL/min (0.81 mol equivalent/1,4-cyclohexanedicarboxylic acid/hr) to increase the temperature to 280° C., and while the temperature was kept constant, reaction was performed. After four hours, the reaction mixture was cooled to room temperature.

The solid product was suspended in methanol, and then the suspension was filtered to remove the catalyst.

The filtrate was analyzed by gas chromatography, and it was found that the conversion of 1,4-cyclohexanedicarboxylic acid was 99.5%, the yield of 1,4-dicyanocyclohexane was 94.7%, and the trans isomer/cis isomer ratio was 58/42.

Next, to 8 g of 1,4-dicyanocyclohexane containing a mixture of the trans isomer and the cis isomer obtained by distilling off the solvent from the filtrate obtained as described above, 18.7 g of 1-butanol was added, and heated to 80° C. to dissolve the 1,4-dicyanocyclohexane. Thereafter, as the mixture was cooled to room temperature, a precipitate was appeared.

The suspension was filtered, and the residue was further washed with 18.7 g of 1-butanol. Thereafter, the residue was dried, and 3.8 g of white solid was obtained (yield 48%).

The obtained white solid was analyzed by gas chromatography, and it was found that the solid was 1,4-dicyanocyclohexane having a purity of 99.5% or more, and the trans isomer/cis isomer ratio was 94/6.

A metal (tin) content of the solid was 10 ppm or less, which is 9.95 (10×0.995) ppm or less relative to 1,4-dicyanocyclohexane (including trans isomer and cis isomer), and 9.35 (9.95×0.94) ppm or less relative to trans-1,4-dicyanocyclohexane.

Meanwhile, the solvent was distilled off from the filtrate after the filtration, and 4.2 g of a yellow solid was obtained. The obtained yellow solid was analyzed by gas chromatography, and it was found that the solid was 1,4-dicyanocyclohexane having a purity of 87%, and the trans isomer/cis isomer ratio was 16/84.

[Aminomethylation Step]

A 100 mL stainless steel-made autoclave equipped with a stirrer was charged with 3.5 g of 1,4-dicyanocyclohexane having a trans isomer/cis isomer ratio of 94/6 obtained in the cyanation step, 0.35 g of a catalyst (manganese-containing Raney cobalt manufactured by Kawaken Fine Chemicals Co., Ltd.), 3.9 mL of a 28 wt % ammonia water, and 7.3 mL of 1-butanol. The autoclave was purged with nitrogen introduced from the autoclave nozzle inlet three times at 2 MPa, and the mixture was heated to 80° C. while stirring at 400 rpm.

When the temperature reached 80° C., hydrogen supply was started intermittently to achieve a pressure of 0.95 MPa, and the reaction was performed until there is no hydrogen absorption.

After the completion of reaction, the product was cooled to room temperature. The reaction mixture was taken out, and was filtered to remove the catalyst.

The filtrate was analyzed by gas chromatography, and it was found that the conversion of 1,4-dicyanocyclohexane was 100%, the yield of 1,4-bis(aminomethyl)cyclohexane was 96%, and the trans isomer/cis isomer ratio was 87/13.

The filtrate was distilled under a reduced pressure of 10 mmHg, and 1,4-bis(aminomethyl)cyclohexane having a purity of 99.5% or more and a trans isomer/cis isomer ratio of 88/12 was obtained with a yield of 97%.

Example 2

Reaction was performed in the same manner as in the cyanation step of Example 1, except that 4.0 g of the yellow solid obtained after the reaction in the cyanation step in Example 1 (3.5 g of 1,4-dicyanocyclohexane) was added to the reactor in the cyanation step.

After 8 hours, the reaction mixture was cooled to room temperature.

The solid product was suspended in methanol, and then the suspension was filtered to remove the catalyst.

The filtrate was analyzed by gas chromatography, and it was found that the conversion of 1,4-cyclohexanedicarboxylic acid was 100%, the yield of 1,4-dicyanocyclohexane was 91.7%, and the trans isomer/cis isomer ratio was 54/46.

[Examination of Nuclear Hydrogenation Step]

Example 3

A 100 mL stainless steel-made autoclave equipped with a stirrer was charged with 12.0 g of terephthalic acid, 1.6 g of a catalyst (5% Pd/C, manufactured by NE Chemcat Corporation), and 28 mL of water. The autoclave was purged with nitrogen introduced from the autoclave nozzle inlet three times at 7 MPa, and the mixture was heated to 150° C. while stirring at 400 rpm.

When the temperature reached 150° C., hydrogen supply was started intermittently to achieve a pressure of 5 MPa, and the reaction was performed until there is no hydrogen absorption.

After the completion of reaction, the mixture was cooled to room temperature. The reaction mixture was taken out, and after a 5N aqueous NaOH solution containing sodium hydroxide of 2.5 times mol the charged terephthalic acid amount was added thereto, the mixture was filtered to remove the catalyst.

The filtrate was neutralized with a 5N aqueous HCl solution, and then analyzed by high-performance liquid chromatography. It was found that the conversion of terephthalic acid was 100%, the yield of 1,4-cyclohexanedicarboxylic acid was 99.5%, and the trans isomer/cis isomer ratio was 34/66.

Example 4

A 100 mL stainless steel-made autoclave equipped with a stirrer was charged with 6.0 g of terephthalic acid, 0.23 g of a catalyst (5% Pd/C, manufactured by NE Chemcat Corporation), and 34 mL of water. The autoclave was purged with nitrogen introduced from the autoclave nozzle inlet three times at 6 MPa, and the mixture was heated to 150° C. while stirring at 400 rpm.

When the temperature reached 150° C., hydrogen supply was started intermittently to achieve a pressure of 4 MPa, and reaction was performed for 5.5 hours.

After the completion of reaction, the mixture was cooled to room temperature. The reaction mixture was taken out, 200 ml of water was added thereto, and the mixture was heated to 90° C. to dissolve the product. Thereafter, the mixture was filtered to remove the catalyst.

The filtrate was analyzed by gas chromatography, and it was found that the conversion of terephthalic acid was 99.5%, the yield of 1,4-cyclohexanedicarboxylic acid was 91.9%, and the trans isomer/cis isomer ratio was 36/64.

Examples 5 to 13

The catalyst removed after filtration in Example 4 was recovered, and reaction was performed repeatedly with the same conditions as those of Example 4. The results are shown in Table 1. The reaction product did not greatly decrease even after ten times of reaction, and 1,4-cyclohexanedicarboxylic acid was obtained with a high yield.

TABLE 1

| | | Reaction | Terephthalic Acid | 1,4-cyclohexanedicarboxylic acid | |
|---|---|---|---|---|---|
| Example No. | Catalyst Used | Time (hr) | Conversion (%) | Yield (%) | cis isomer/trans isomer ratio |
| Example 4 | 5%Pd/C | 5.5 | 99.5 | 91.9 | 36/64 |
| Example 5 | Catalyst Recovered in Example 4 | 6 | 98.6 | 95.2 | 34/66 |
| Example 6 | Catalyst Recovered in Example 5 | 6 | 100 | 94.8 | 34/66 |
| Example 7 | Catalyst Recovered in Example 6 | 4.5 | 100 | 87.7 | 34/66 |
| Example 8 | Catalyst Recovered in Example 7 | 4.5 | 100 | 91.2 | 34/66 |
| Example 9 | Catalyst Recovered in Example 8 | 5 | 100 | 93.2 | 34/66 |
| Example 10 | Catalyst Recovered in Example 9 | 5 | 100 | 91.7 | 36/64 |
| Example 11 | Catalyst Recovered in Example 10 | 5.5 | 100 | 95.7 | 36/64 |
| Example 12 | Catalyst Recovered in Example 11 | 6 | 100 | 96.8 | 37/63 |
| Example 13 | Catalyst Recovered in Example 12 | 6.5 | 100 | 91.7 | 36/64 |

Examination of Cyanation Step

Example 14

A four-neck flask equipped with a stirrer, a gas inlet tube, a thermometer, a gas purge line, and a condenser was charged with 153 g of 1,4-cyclohexanedicarboxylic acid obtained in the same manner as in Example 3, 17.5 g of dimethyl 1,4-cyclohexanedicarboxylate, and 0.39 g of tin (II) oxide, and the mixture was heated to 210° C. while stirring at 250 rpm.

Thereafter, ammonia gas was introduced at a rate of 72 mL/min (1.1 mol equivalent/1,4-cyclohexanedicarboxylic acid+dimethyl 1,4-cyclohexanedicarboxylate/hr) and the temperature in the reactor was kept at 210° C. for 1 hour. Then the temperature was increased to 280° C., and while the temperature was kept constant, reaction was performed. After 8 hours, the reaction mixture was cooled to room temperature. When the reaction was terminated, a white solid was observed in the gas purge line and the condenser.

The solid product and the white solid observed in the gas purge line and the condenser were together suspended in methanol, and then the suspension was filtered to remove the catalyst.

The filtrate was analyzed by gas chromatography, and it was found that the conversion of 1,4-cyclohexanedicarboxylic acid was 100%, the conversion of dimethyl 1,4-cyclohexanedicarboxylate was 100%, the yield of 1,4-dicyanocyclohexane was 90.2%, and the trans isomer/cis isomer ratio was 53/47.

Example 15

A four-neck flask equipped with a stirrer, a gas inlet tube, a thermometer, a gas purge line, and a condenser was charged with 15.1 g of 1,4-cyclohexanedicarboxylic acid obtained in the same manner as in Example 3, 17.4 g of dimethyl 1,4-cyclohexanedicarboxylate, 4.9 g of N,N'-dimethylimidazolidinone (boiling point 226° C.), and 0.40 g of tin (II) oxide, and the mixture was heated to 210° C. while stirring at 250 rpm.

Thereafter, ammonia gas was introduced at a rate of 72 mL/min (1.1 mol equivalent/1,4-cyclohexanedicarboxylic acid+dimethyl 1,4-cyclohexanedicarboxylate/hr) and the temperature in the reactor was kept at 210° C. for 1 hour. Then the temperature was increased to 280° C., and while the temperature was kept constant, reaction was performed. After 8 hours, the reaction mixture was cooled to 90° C. When the reaction was terminated, almost no white solid was observed in the gas purge line and the condenser.

Then, 31.6 g of 1-butanol was added thereto and the mixture was stirred to produce a reaction mixture. The reaction mixture was filtered by hot filtration to remove the catalyst. The filtrate was analyzed by gas chromatography, and it was found that the conversion of 1,4-cyclohexanedicarboxylic acid was 100%, the conversion of dimethyl 1,4-cyclohexanedicarboxylate was 99.9%, the yield of 1,4-dicyanocyclohexane was 89%, and the trans isomer/cis isomer ratio was 53/47.

Next, 12.6 g of 1-butanol was added to 37.3 g of the filtrate obtained as described above at 90° C., and as the mixture was cooled while stirring to room temperature, a precipitate was appeared. The suspension was filtered, and the residue was further washed twice with 17.5 g of 1-butanol. Thereafter, the residue was dried, thereby producing 6.7 g of a light yellow solid (yield 45%).

The obtained light yellow solid was analyzed by gas chromatography, and it was found that the solid was 1,4-dicyanocyclohexane having a purity of 99.5% or more, and the trans isomer/cis isomer ratio was 95/5.

A metal (tin) content of the solid was 1 ppm or less, which is 0.995 (1×0.995) ppm or less relative to 1,4-dicyanocyclohexane (including trans isomer and cis isomer) and 0.945 (0.995×0.95) ppm or less relative to trans-1,4-dicyanocyclohexane.

Meanwhile, the solvent was distilled off from the filtrate after the filtration and washings, and 7.0 g of a yellow solid was obtained. The obtained yellow solid was analyzed by gas chromatography, and it was found that the solid was 1,4-dicyanocyclohexane having a purity of 89%, and the trans isomer/cis isomer ratio was 13/87.

Example 16

13.5 g of a yellow solid obtained in the same manner as in Example 15 (12.0 g of 1,4-dicyanocyclohexane) was added to the reactor in the cyanation step, and reaction was performed in the same manner as in Example 15, except that dimethyl 1,4-cyclohexanedicarboxylate was not added, and the rate of the ammonia gas introduction was changed to 36 mL/min (1.1 mol equivalent/1,4-cyclohexanedicarboxylic acid/hr).

After 15 hours, the reaction mixture was treated in the same manner as in Example 15.

As a result of gas chromatography analysis, it was found that the conversion of 1,4-cyclohexanedicarboxylic acid was 100%, the yield of 1,4-dicyanocyclohexane was 94.5%, and the trans isomer/cis isomer ratio was 53/47. The cyanation reaction proceeded with high yields even if the recovered solid mainly composed of the separated cis-1,4-dicyanocyclohexane was fed again in the cyanation step.

Example 17

Reaction was performed in the same manner as in Example 15, except that 3.3 g of tetraethylene glycol dimethylether (boiling point 275° C.) was used instead of 4.9 g of N,N-dimethylimidazolidinone. When the reaction was terminated, almost no white solid was observed in the gas purge line and the condenser.

The reaction mixture was filtered by hot filtration in the same manner as in Example 15. The filtrate was analyzed by gas chromatography, and it was found that the conversion of 1,4-cyclohexanedicarboxylic acid was 100%, the conversion of dimethyl 1,4-cyclohexanedicarboxylate was 100%, the yield of 1,4-dicyanocyclohexane was 87%, and the trans isomer/cis isomer ratio was 52/48.

Example 18

Reaction was performed in the same manner as in Example 15, except that 3.3 g of triethylene glycol dimethylether (boiling point 216° C.) was used instead of 4.9 g of N,N'-dimethylimidazolidinone. When the reaction was terminated, almost no white solid was observed in the gas purge line and the condenser.

The reaction mixture was filtered by hot filtration in the same manner as in Example 15. The filtrate was analyzed by gas chromatography, and it was found that the conversion of 1,4-cyclohexanedicarboxylic acid was 100%, the conversion of dimethyl 1,4-cyclohexanedicarboxylate was 100%, the yield of 1,4-dicyanocyclohexane was 85%, and the trans isomer/cis isomer ratio was 51/49.

Example 19

A four-neck flask equipped with a stirrer, a gas inlet tube, a thermometer, a gas purge line, and a condenser was charged with 42.2 g of commercially available 1,4-cyclohexanedicarboxylic acid, 49.1 g of dimethyl 1,4-cyclohexanedicarboxylate, 13.7 g of N,N'-dimethylimidazolidinone, and 1.06 g of tin (II) oxide, and the mixture was heated to 210° C. while stirring at 250 rpm.

Thereafter, ammonia gas and nitrogen were mixedly introduced at a rate of 100 mL/min (0.55 mol equivalent/1,4-cyclohexanedicarboxylic acid+dimethyl 1,4-cyclohexanedicarboxylate/hr) and a rate of 100 mL/min, respectively. The temperature of the reactor was kept at 210° C. for 1 hour, then increased to 280° C., and while the temperature was kept constant, reaction was performed. After 16 hours, the reaction mixture was cooled to 90° C. When the reaction was terminated, almost no white solid was observed in the gas purge line and the condenser.

Then, 100 g of 1-butanol was added thereto and stirred. The reaction mixture was filtered by hot filtration to remove the catalyst. The filtrate was analyzed by gas chromatography, and it was found that the conversion of 1,4-cyclohexanedicarboxylic acid was 100%, the conversion of dimethyl 1,4-cyclohexanedicarboxylate was 98.8%, the yield of 1,4-dicyanocyclohexane was 86.0%, and the trans isomer/cis isomer ratio was 52/48.

Next, as the filtrate obtained as described above was cooled while stirring to room temperature, a precipitate was appeared. The suspension liquid was filtered, and the residue was further washed with 50 g of 1-butanol twice. Thereafter, the residue was dried, thereby producing a light yellow solid. The obtained light yellow solid was analyzed by gas chromatography, and it was found that the solid was 1,4-dicyanocyclohexane having a purity of 96.9%, and the trans isomer/cis isomer ratio was 89/11.

A metal (tin) content of the solid was 4.3 ppm, which is 4.17 (4.3×0.969) ppm relative to 1,4-dicyanocyclohexane (including trans isomer and cis isomer) and 3.7 (4.17×0.89) ppm relative to trans-1,4-dicyanocyclohexane.

Meanwhile, the solvent was distilled off from the filtrate after the filtration and washings, and a yellow solid was obtained. The obtained yellow solid was analyzed by gas chromatography, and it was found that the solid was 1,4-dicyanocyclohexane having a purity of 90%, and the trans isomer/cis isomer ratio was 21/79.

Example 20

Reaction was performed in the same manner as in Example 19, except that 35.2 g of the yellow solid obtained in Example 19 was added to the reactor in the cyanation step, and dimethyl 1,4-cyclohexanedicarboxylate was not added.

After 16 hours, and the reaction mixture was treated in the same manner as in Example 19.

As a result of gas chromatography analysis, it was found that the conversion of 1,4-cyclohexanedicarboxylic acid was 100%, the yield of 1,4-dicyanocyclohexane was 93.4%, and the trans isomer/cis isomer ratio was 52/48. The cyanation reaction proceeded with high yields even if the recovered solid mainly composed of the separated cis-1,4-dicyanocyclohexane was fed again in the cyanation step.

Furthermore, the product was filtered by hot filtration and cooled; and the appeared precipitant was filtered, washed, and dried in the same manner as in Example 19, thereby producing a light yellow solid. The obtained light yellow solid was analyzed by gas chromatography, and it was found that the solid was 1,4-dicyanocyclohexane having a purity of 93%, and the trans isomer/cis isomer ratio was 95/5.

A metal (tin) content of the solid was 44 ppm, which is 40.9 ppm (44×0.93) relative to 1,4-dicyanocyclohexane (including trans isomer and cis isomer) and 38.8 ppm (40.9×0.95) relative to trans-1,4-dicyanocyclohexane.

Example 21

A four-neck flask equipped with a stirrer, a gas inlet tube, a thermometer, a gas purge line, and a condenser was charged with 143.3 g of commercially available 1,4-cyclohexanedicarboxylic acid, 166.7 g of dimethyl 1,4-cyclohexanedicarboxylate, 55.7 g of N,N'-dimethylimidazolidinone, and 3.6 g tin (II) oxide. Ammonia gas and nitrogen were mixedly introduced thereto at a rate of 90 mL/min (0.14 mol equivalent/1,4-cyclohexanedicarboxylic acid+dimethyl 1,4-cyclohexanedicarboxylate/hr) and 10 mL/min, respectively. The temperature was increased to 280° C., and while the temperature was kept constant, reaction was performed. After 48 hours, the reaction mixture was cooled to 90° C. When the reaction was terminated, almost no white solid was observed in the gas purge line and the condenser.

70 g of 1-butanol was added to 30 g of the mixture and stirred. The reaction mixture was filtered by hot filtration to remove the catalyst. The filtrate was analyzed by gas chromatography, and it was found that the yield of 1,4-dicyanocyclohexane was 86%.

The remaining of the mixture was filtered by hot filtration in the same manner as in Example 15, cooled, and the appeared precipitant was filtered, washed, and dried, thereby producing a light yellow solid. The obtained light yellow solid was analyzed by gas chromatography, and it was found that the solid was 1,4-dicyanocyclohexane having a purity of 95.7%, and the trans isomer/cis isomer ratio was 95/5.

A metal (tin) content of the solid was 10 ppm or less, which is 9.57 ppm or less (10×0.957) relative to 1,4-dicyanocyclohexane (including trans isomer and cis isomer) and 9.09 ppm or less (9.57×0.95) relative to trans-1,4-dicyanocyclohexane.

Comparative Example 1

Reaction was performed in the same manner as in Example 21, except that the ammonia gas feeding rate was set to an average of 49 mL/min (0.076 mol equivalent/1,4-cyclohexanedicarboxylic acid+dimethyl 1,4-cyclohexanedicarboxylate/hr), and the reaction time was set to 80 hours. The yield of 1,4-dicyanocyclohexane was 68%. The mixture was filtered by hot filtration and cooled; and the appeared precipitant was filtered, washed, and dried in the same manner as Example 15, thereby producing a light yellow solid. The obtained light yellow solid was analyzed by gas chromatography, and it was found that the solid was 1,4-dicyanocyclohexane having a purity of 94%, and the trans isomer/cis isomer ratio was 95/5.

A metal (tin) content of the solid was 3800 ppm (0.38%), which is 3572 ppm (3800×0.94) relative to 1,4-dicyanocyclohexane (including trans isomer and cis isomer), and 3393 ppm (3572×0.95) relative to trans-1,4-dicyanocyclohexane.

Example 22

32.5 g of the trans-1,4-dicyanocyclohexane obtained in Comparative Example 1 and 315 g of methanol were dissolved at 60° C., and 0.7 g of activated carbon (manufactured by Wako Pure Chemical Industries, Ltd.) was added thereto. The mixture was stirred for 2 hours. The mixture was filtered at 60° C. to remove the activated carbon, and the solvent was distilled off from the filtrate, thereby producing 32.1 g of white solid. The obtained white solid was analyzed by gas chromatography, and it was found that the solid was 1,4-dicyanocyclohexane having a purity of 96.4%, and the trans isomer/cis isomer ratio was 95/5.

A metal (tin) content of the solid was 130 ppm, which is 125 ppm (130×0.964) relative to 1,4-dicyanocyclohexane (including trans isomer and cis isomer), and 119 ppm (125×0.95) relative to trans-1,4-dicyanocyclohexane.

Example 23

The treatment was performed in the same manner as in Example 22, except that activated carbon was not used. The obtained light yellow solid was analyzed by gas chromatography, and it was found that the solid was 1,4-dicyanocyclohexane having a purity of 95.8%, and the trans isomer/cis isomer ratio was 95/5.

A metal (tin) content of the solid was 1200 ppm (0.12%), which is 1150 ppm (1200×0.94) relative to 1,4-dicyanocyclohexane (including trans isomer and cis isomer), and 1092 ppm (1150×0.95) relative to trans-1,4-dicyanocyclohexane.

Example 24

Reaction was performed in the same manner as in Example 14, except that ammonia gas was introduced at a rate of 48 mL/min (0.73 mol equivalent/1,4-cyclohexanedicarboxylic acid+dimethyl 1,4-cyclohexanedicarboxylate/hr). When the reaction was terminated, a white solid was observed in the gas purge line and the condenser.

The solid product and the white solid observed in the gas purge line and the condenser were together treated in the same manner as in Example 14. The filtrate was analyzed by gas chromatography, and it was found that the conversion of 1,4-cyclohexanedicarboxylic acid was 100%, the conversion of dimethyl 1,4-cyclohexanedicarboxylate was 99%, the yield of 1,4-dicyanocyclohexane was 84%, and the trans isomer/cis isomer ratio was 54/46.

Example 25

Reaction was performed in the same manner as in Example 14, except that ammonia gas was introduced at a rate of 24 mL/min (0.36 mol equivalent/1,4-cyclohexanedicarboxylic acid+dimethyl 1,4-cyclohexanedicarboxylate/hr). When the reaction was terminated, a white solid was observed in the gas purge line and the condenser.

The solid product and the white solid observed in the gas purge line and the condenser were together treated in the same manner as in Example 14. The filtrate was analyzed by gas chromatography, and it was found that conversion of dimethyl 1,4-cyclohexanedicarboxylate was 98%, the yield of 1,4-dicyanocyclohexane was 54%, and the trans isomer/cis isomer ratio was 52/48.

Examination of Aminomethylation Step

Example 26

A 100 mL stainless steel-made autoclave equipped with a stirrer was charged with 5.5 g of 1,4-dicyanocyclohexane having a trans isomer/cis isomer ratio of 96/4 obtained in the same manner as in Example 15, 0.3 g of a catalyst (Raney nickel manufactured by Kawaken Fine Chemicals Co., Ltd.), 5.6 mL of a 28 wt % ammonia water, and 10.5 mL of 1-butanol. The autoclave was purged with nitrogen introduced from the autoclave nozzle inlet three times at 2 MPa, and the mixture was heated to 80° C. while stiffing at 400 rpm.

When the temperature reached 80° C., hydrogen supply was started intermittently to achieve a pressure of 0.95 MPa, and the reaction was performed until there is no hydrogen absorption.

After the completion of reaction, the mixture was cooled to room temperature. The reaction mixture was taken out, and was filtered to remove the catalyst.

The filtrate was analyzed by gas chromatography, and it was found that the conversion of 1,4-dicyanocyclohexane was 100%, the yield of 1,4-bis(aminomethyl)cyclohexane was 99%, and the trans isomer/cis isomer ratio was 88/12.

The reaction mixture was distilled under a reduced pressure of 10 mmHg, and 1,4-bis(aminomethyl)cyclohexane having a trans isomer/cis isomer ratio of 86/14 and a purity of 99.5% or more was obtained with a yield of 95%.

Example 27

A 100 mL stainless steel-made autoclave equipped with a stirrer was charged with 5.3 g of trans-1,4-dicyanocyclohexane (purity 99.5% or more, trans isomer/cis isomer ratio=95/5, tin content 1 ppm or less) obtained in the same manner as in Example 15, 0.26 g of a catalyst (manganese-containing Raney cobalt manufactured by Kawaken Fine Chemicals Co., Ltd.), 6.4 mL of a 28 wt % ammonia water, and 10.8 mL of 1-butanol. The autoclave was purged with nitrogen introduced from the autoclave nozzle inlet three times at 5 MPa, and the mixture was heated to 80° C. while stirring at 400 rpm.

When the temperature reached 80° C., hydrogen supply was started intermittently to achieve a pressure of 3.5 MPa, and the reaction was performed until there is no hydrogen absorption. The reaction time was 3 hours.

After the completion of reaction, the mixture was cooled to room temperature. The reaction mixture was taken out, and was filtered to remove the catalyst.

The filtrate was analyzed by gas chromatography, and it was found that the conversion of 1,4-dicyanocyclohexane was 96.3%, the yield of 1,4-bis(aminomethyl)cyclohexane was 94.3%, and the trans isomer/cis isomer ratio was 93/7.

Examples 28 to 31

The catalyst removed after filtration in Example 23 was recovered, and reaction was performed repeatedly with the same conditions as those of Example 27. The results are shown in Table 2. The reaction product did not greatly decrease even after five times of reaction, and trans-1,4-bis(aminomethyl)cyclohexane was obtained with high yields.

TABLE 2

| Example No. | Catalyst Used | Reaction Time (hr) | 1,4-dicyano-cyclohexane Conversion (%) | 1,4-bis(aminomethyl)cyclohexane Yield (%) | 1,4-bis(aminomethyl)cyclohexane trans isomer/cis isomer ratio |
|---|---|---|---|---|---|
| Example 27 | Manganese-containing Raney cobalt | 3 | 96.3 | 94.3 | 93/7 |
| Example 28 | Catalyst Recovered in Example 27 | 3 | 96.4 | 91.4 | 93/7 |
| Example 29 | Catalyst Recovered in Example 28 | 3.5 | 96.3 | 96.1 | 93/7 |
| Example 30 | Catalyst Recovered in Example 29 | 3.5 | 96 | 89.4 | 93/7 |
| Example 31 | Catalyst Recovered in Example 30 | 4 | 96.6 | 92.8 | 93/7 |

Example 32

A 100 mL stainless steel-made autoclave equipped with a stirrer was charged with 9.0 g of trans-1,4-dicyanocyclohexane (purity 99.5% or more, trans isomer/cis isomer ratio=94/6, tin content 1 ppm or less) obtained in the same manner as in Example 15, 0.45 g of a catalyst (manganese-containing Raney cobalt manufactured by Kawaken Fine Chemicals Co., Ltd.), 4.6 mL of a 28 wt % ammonia water, and 14.6 mL of methanol. The autoclave was purged with nitrogen introduced from the autoclave nozzle inlet three times at 5 MPa, and the mixture was heated to 80° C. while stiffing at 400 rpm.

When the temperature reached 80° C., hydrogen supply was started intermittently to achieve a pressure of 4.5 MPa, and reaction was performed for 2.5 hours.

After the completion of reaction, the mixture was cooled to room temperature. The reaction mixture was taken out, and was filtered to remove the catalyst.

The filtrate was analyzed by gas chromatography, and it was found that the conversion of 1,4-dicyanocyclohexane was 95.2%, the yield of 1,4-bis(aminomethyl)cyclohexane was 89.2%, and the trans isomer/cis isomer ratio was 93/7.

Examples 33 to 37 and Comparative Example 2

Reaction was performed in the same manner as in Example 32, except that trans-1,4-dicyanocyclohexane used was changed as shown in Table 3. The results are shown in Table 3. When trans-1,4-dicyanocyclohexane having a smaller tin content was used, 1,4-bis(aminomethyl)cyclohexane was produced with a high yield.

TABLE 3

| Ex. and | trans-1,4-dicyanocyclohexane | | | 1,4-bis(aminomethyl)cyclohexane | |
|---|---|---|---|---|---|
| Comp. Ex. No. | Production Method | Metal Content (ppm) | Conversion (%) | Yield (%) | trans isomer/cis isomer ratio |
| Example 32 | Example 15 | 0.945 | 95.2 | 89.2 | 93/7 |
| Example 33 | Example 19 | 3.7 | >99 | >99 | 89/11 |
| Example 34 | Example 20 | 38.8 | >99 | >99 | 92/8 |
| Example 35 | Example 21 | 9.09 | >99 | 95.1 | 88/12 |
| Comp. Ex. 2 | Comp. Ex. 1 | 3393 | 80.8 | 25.9 | 95/5 |
| Example 36 | Example 22 | 119 | 94.5 | 87.7 | 92/8 |
| Example 37 | Example 23 | 1092 | 91.6 | 62.3 | 95/5 |

Cyanation: Comparison of Reactions with Different ammonia Gas Flow Rate

Example 38

A four-neck flask equipped with a stirrer, a gas inlet tube, a thermometer, a gas purge line, and a condenser was charged with 287 g of commercially available 1,4-cyclohexanedicarboxylic acid, 55.7 g of N,N'-dimethylimidazolidinone, and 3.6 g of tin (II) oxide, and ammonia gas and nitrogen were mixedly introduced thereto at a rate of 43 mL/min (0.07 mol equivalent/1,4-cyclohexanedicarboxylic acid/hr), and 5 mL/min, respectively. The temperature was increased to 280° C., and while the temperature was kept constant, reaction was performed. After 60 hours, the reaction mixture was cooled to 90° C. When the reaction was terminated, almost no white solid was observed in the gas purge line and the condenser.

70 g of 1-butanol was added to 30 g of the product and stirred. The reaction mixture was filtered by hot filtration to remove the catalyst. The filtrate was analyzed by gas chromatography, and it was found that the yield of 1,4-dicyanocyclohexane was 70%.

Examples 39 to 41

Reaction was performed in the same manner as in Example 38, except that the rate of ammonia gas and nitrogen supply and the reaction time were changed. The results are shown in Table 4.

TABLE 4

| Example No. | Ammonia Gas Feeding Rate (mL/min) | Nitrogen Feeding Rate (mL/min) | Reaction Time (hr) | 1,4-dicyano-cyclohexane Yield (%) |
|---|---|---|---|---|
| Example 38 | 43 | 5 | 60 | 70 |
| Example 39 | 90 | 10 | 48 | 85 |
| Example 40 | 180 | 20 | 32 | 90 |
| Example 41 | 360 | 40 | 20 | 91 |

Example 42

A four-neck flask equipped with a stirrer, a gas inlet tube, a thermometer, a gas purge line, and a condenser was charged with 74 g of commercially available 1,4-cyclohexanedicarboxylic acid, 14.8 g of N,N'-dimethylimidazolidinone, and 0.93 g of tin (II) oxide, and ammonia gas and nitrogen were mixedly introduced thereto at a rate of 135 mL/min (0.84 mol equivalent/1,4-cyclohexanedicarboxylic acid/hr), and 15 mL/min, respectively. The temperature was increased to 280° C., and while the temperature was kept constant, reaction was performed. After 13 hours, the reaction mixture was cooled to 90° C. When the reaction was terminated, almost no white solid was observed in the gas purge line and the condenser.

70 g of 1-butanol was added to 30 g of the product and stirred. The reaction mixture was filtered by hot filtration to remove the catalyst. The filtrate was analyzed by gas chromatography, and it was found that the yield of 1,4-dicyanocyclohexane was 91%.

Example 43

Reaction was performed in the same manner as in Example 42, except that the rate of ammonia gas and nitrogen supply was set to 180 mL/min and 20 mL/min, respectively, and the reaction time was set to 9 hours. The yield of 1,4-dicyanocyclohexane was 93%.

These Examples show that the greater the ammonia gas feeding rate is, the shorter the reaction time is and the higher the yield of 1,4-dicyanocyclohexane is.

Cyanation: Comparison of Reactions with Different Metal Oxides

Examples 44 to 49 and Comparative Example 3

Reaction was performed in the same manner as in Example 42, except that the metals and amounts of metal oxide used were changed as shown in Table 5 from 0.93 g of tin (II) oxide, and the reaction time was also changed. The results are shown in Table 5.

TABLE 5

| Ex. and Comp. Ex. No. | Metal Oxide Type | Metal Oxide Amount Used(g) | Reaction Time (hr) | 1,4-dicyano-cyclohexane Yield (%) |
|---|---|---|---|---|
| Example 42 | Tin (II) Oxide | 0.93 | 13 | 91 |
| Example 44 | Zinc Oxide | 0.56 | 16 | 92 |
| Example 45 | Cobalt (III) Oxide | 1.14 | 14 | 86 |
| Example 46 | Iron (III) Oxide | 1.11 | 14 | 91 |
| Example 47 | Manganese Dioxide | 0.60 | 16 | 89 |
| Example 48 | Vanadium Pentoxide | 1.26 | 18 | 93 |
| Example 49 | Titanium Dioxide | 0.55 | 15 | 89 |
| Comp. Ex. 3 | None | — | 26 | 78 |

These Examples show that metal oxides accelerate the reaction.

Cyanation: Changes in Solvent

Example 50

Reaction was performed in the same manner as in Example 42, except that 12.9 g of N-methyl-2-pyrrolidinone (boiling point 202° C.) was used instead of 14.8 g of N,N'-dimethylimidazolidinone. When the reaction was terminated, almost no white solid was observed in the gas purge line and the condenser.

70 g of 1-butanol was added to 30 g of the product and stirred. The reaction mixture was filtered by hot filtration to remove the catalyst. The filtrate was analyzed by gas chromatography, and it was found that the yield of 1,4-dicyanocyclohexane was 91%.

Cyanation: Recycling of Metal Oxide Catalyst

Examples 52 to 53

In Example 42, the remaining of the mixture was also filtered by hot filtration in the same manner as in Example 42 to separate the catalyst. The separated catalyst was recovered together with 30 g of the previously filtered product by hot filtration. The recovered catalyst was used repeatedly instead of 0.93 g of tin (II) oxide, and reaction was performed in the same manner as in Example 42. The results are shown in Table 6. The reaction product did not greatly decrease even after three times of reaction, and 1,4-dicyanocyclohexane was obtained with a high yield.

TABLE 6

| Example No. | Catalyst (Metal Oxide) | Reaction Time (hr) | 1,4-dicyanocyclohexane Yield (%) |
|---|---|---|---|
| Example 42 | Tin (II) oxide | 13 | 91 |
| Example 52 | Catalyst Recovered in Example 42 | 13 | 90 |
| Example 53 | Catalyst Recovered in Example 52 | 13 | 90 |

Cyanation: Isomerization of 1,4-dicyanocyclohexane in the Absence of Hydrogenated Carboxylic Acid Derivative Example 54

78.1 g of 1-butanol was added to the product obtained in the same manner as in Example 42 and stirred. The reaction mixture was filtered by hot filtration to remove the catalyst. The filtrate was analyzed by gas chromatography, and it was found that the yield of 1,4-dicyanocyclohexane was 89%, and the trans isomer/cis isomer ratio was 53/47.

Next, 31 g of 1-butanol was added to 92 g of the filtrate obtained as described above at 90° C., and as the reaction mixture was cooled to room temperature while stirring, a precipitate was appeared. The suspension was filtered, and the residue was further washed with 43.2 g of 1-butanol twice. Thereafter, the residue was dried, thereby producing 16.5 g of a light yellow solid (yield 45%).

The obtained light yellow solid was analyzed by gas chromatography, and it was found that the solid was 1,4-dicyanocyclohexane having a purity of 99.5% or more, and the trans isomer/cis isomer ratio was 96/4.

A metal (tin) content of the solid was 1 ppm or less, which is 0.995 (1×0.995) ppm or less relative to 1,4-dicyanocyclohexane (including trans isomer and cis isomer) and 0.955 (0.995×0.96) ppm or less relative to trans-1,4-dicyanocyclohexane.

Meanwhile, the solvent was distilled off from the filtrate after the filtration and washings, and 17.3 g of a yellow solid was obtained. The obtained yellow solid was analyzed by gas chromatography, and it was found that the solid was 1,4-dicyanocyclohexane having a purity of 90%, and the trans isomer/cis isomer ratio was 13/87.

Using the thus obtained 1,4-dicyanocyclohexane having a high cis isomer ratio, thermal isomerization reaction was performed in the absence of hydrogenated carboxylic acid or a derivative thereof.

Example 55

A four-neck flask equipped with a stirrer, a gas inlet tube, a thermometer, a gas purge line, and a condenser was charged with 3 g of 1,4-dicyanocyclohexane (purity 90%, trans isomer/cis isomer ratio 13/87) having a high cis isomer ratio obtained in the same manner as in Example 54, and 0.8 g of N,N'-dimethylimidazolidinone. Ammonia gas was introduced thereto while stirring at a rate of 17 mL/min (0.2 mol equivalent/1,4-dicyanocyclohexane/hr) to increase the temperature to 280° C., and while the temperature was kept constant, reaction was performed for 10 hours, and then cooled. The obtained product was analyzed by gas chromatography, and it was found that 1,4-dicyanocyclohexane had a purity of 90% (1,4-dicyanocyclohexane recovery of 99% or more), and the trans isomer/cis isomer ratio was 53/47.

Examples 56 to 58

Reaction was performed in the same manner as in Example 55, except that use or non-use of tin (II) oxide, and ammonia gas feeding rate were changed. The results are shown in Table 7.

TABLE 7

| Example No. | Tin (II) Oxide Amount Used(g) | Ammonia Gas Feeding Rate (mL/min) | Reaction Time (hr) | 1,4-dicyano-cyclohexane Purity(%) | 1,4-dicyano-cyclohexane trans isomer/cis isomer ratio |
|---|---|---|---|---|---|
| Example 55 | 0 | 17 | 10 | 90 | 53/47 |
| Example 56 | 0 | 68 | 10 | 90 | 53/47 |
| Example 57 | 0 | 0 | 20 | 90 | 53/47 |
| Example 58 | 0.5 | 0 | 20 | 89 | 53/47 |

These Examples show that, thermal isomerization reaction progresses in the absence of hydrogenated carboxylic acid or a derivative thereof.

Aminomethylation: Relationships Between Remaining Amount of Metal Other than Tin and Reaction Product Example 59

78 g of 1-butanol was added to the product obtained in the same manner as in Example 44 and stirred. The reaction mixture was filtered by hot filtration to remove the catalyst. The filtrate was analyzed by gas chromatography, and it was found that the yield of 1,4-dicyanocyclohexane was 92%, and the trans isomer/cis isomer ratio was 53/47.

Next, 31 g of 1-butanol was added to 92 g of the filtrate obtained as described above at 90° C., and as the reaction product was cooled while stirring to room temperature, a precipitate was appeared. The suspension liquid was filtered, and the residue was further washed with 42 g of 1-butanol twice. Thereafter, the residue was dried, thereby producing 17 g of a light yellow solid (yield 46%).

The obtained light yellow solid was analyzed by gas chromatography, and it was found that the solid was 1,4-dicyanocyclohexane having a purity of 99.5% or more, and the trans isomer/cis isomer ratio was 93/7.

The metal (zinc) content of the solid was 340 ppm, which is 338 (340×0.995) ppm relative to 1,4-dicyanocyclohexane (including trans isomer and cis isomer) and 315 (338×0.93) ppm relative to trans-1,4-dicyanocyclohexane.

Comparative Example 4

Reaction was performed in the same manner as in Example 44, except that the reaction time was set to 12 hours. The yield of 1,4-dicyanocyclohexane was 82%. The mixture was filtered by hot filtration and cooled; and the appeared precipitant was filtered, washed, and dried in the same manner as in Example 59, thereby producing a light yellow solid. The obtained light yellow solid was analyzed by gas chromatography, and it was found that the solid was 1,4-dicyanocyclohexane having a purity of 99%, and the trans isomer/cis isomer ratio was 94/6.

The metal (zinc) content of the solid was 10000 ppm (1.0%), which is 9900 ppm (10000×0.99) relative to 1,4-dicyanocyclohexane (including trans isomer and cis isomer) and 9306 ppm (9900×0.94) relative to trans-1,4-dicyanocyclohexane.

Example 60

The mixture obtained in the same manner as in Example 46 was filtered by hot filtration and cooled; and the appeared precipitant was filtered, washed, and dried in the same manner as in Example 59, thereby producing a light yellow solid. The obtained light yellow solid was analyzed by gas chromatography, and it was found that the solid was 1,4-dicyanocyclohexane having a purity of 99.5% or more, and the trans isomer/cis isomer ratio was 91/9. The metal (iron) content of the solid was 21 ppm, which is 21 (21×0.995) ppm relative to 1,4-dicyanocyclohexane (including trans isomer and cis isomer) and 19 (21×0.91) ppm relative to trans-1,4-dicyanocyclohexane.

Example 61

The mixture obtained in the same manner as in Example 46 was filtered by hot filtration and cooled; and the appeared precipitant was filtered, washed, and dried in the same manner as in Example 59, except that washing with 1-butanol was performed once, thereby producing a light yellow solid. The obtained light yellow solid was analyzed by gas chromatography, and it was found that the solid was 1,4-dicyanocyclohexane having a purity of 99.5% or more, and the trans isomer/cis isomer ratio was 93/7. The metal (iron) content of the solid was 350 ppm, which is 348 (350×0.995) ppm relative to 1,4-dicyanocyclohexane (including trans isomer and cis isomer) and 324 (348×0.93) ppm relative to trans-1,4-dicyanocyclohexane.

Comparative Example 5

Reaction was performed in the same manner as in Example 46, except that the reaction time was set to 12 hours. The yield of 1,4-dicyanocyclohexane was 84%. The mixture was filtered by hot filtration and cooled; and the appeared precipitant was filtered, washed, and dried in the same manner as in Example 59, thereby producing a light yellow solid. The obtained light yellow solid was analyzed by gas chromatography, and it was found that the solid was 1,4-dicyanocyclohexane having a purity of 99.5% or more, and the trans isomer/cis isomer ratio was 92/8.

The metal (iron) content of the solid was 3500 ppm (0.35%), which is 3483 ppm (3500×0.995) relative to 1,4-dicyanocyclohexane (including trans isomer and cis isomer) and 3204 ppm (3483×0.92) relative to trans-1,4-dicyanocyclohexane.

Example 62

A 100 mL stainless steel-made autoclave equipped with a stirrer was charged with 9.0 g of trans-1,4-dicyanocyclohexane (purity 99.5% or more, trans isomer/cis isomer ratio=96/4, tin content 1 ppm or less) obtained in Example 54, 0.45 g of a catalyst (manganese-containing Raney cobalt manufactured by Kawaken Fine Chemicals Co., Ltd.), 14.6 g of a solution of ammonia in methanol (containing 2.4 g of ammonia), and 0.7 g of water. The autoclave was purged with nitrogen introduced from the autoclave nozzle inlet three times at 5 MPa, and the mixture was heated to 80° C. while stirring at 400 rpm.

When the temperature reached 80° C., hydrogen supply was started continuously to achieve a pressure of 4.5 MPa, and the reaction was performed under a constant pressure until there is no hydrogen absorption.

After the completion of reaction, the mixture was cooled to room temperature. The reaction mixture was taken out, and was filtered to remove the catalyst.

The filtrate was analyzed by gas chromatography, and it was found that the conversion of 1,4-dicyanocyclohexane was 99.1%, the yield of 1,4-bis(aminomethyl)cyclohexane was 96.6%, and the trans isomer/cis isomer ratio was 93/7.

Examples 63 to 65 and Comparative Examples 6 to 7

Reaction was performed in the same manner as in Example 62, except that trans-1,4-dicyanocyclohexane used was changed as shown in Table 8. The results are shown in Table 8. When trans-1,4-dicyanocyclohexane having a smaller metal content was used, 1,4-bis(aminomethyl)cyclohexane was produced with a high yield.

TABLE 8

| Ex. and | trans-1,4-dicyanocyclohexane | | Reaction | 1,4-bis(aminomethyl)cyclohexane | | |
|---|---|---|---|---|---|---|
| Comp. Ex. No. | Production Method | Metal Content(ppm) | Conversion (%) | Time hr | Yield (%) | trans isomer/cis isomer ratio |
| Example 62 | Example 54 | tin 0.955 | 99.1 | 2.5 | 96.6 | 93/7 |
| Example 63 | Example 59 | zinc 315 | 98.7 | 4.5 | 93.6 | 93/7 |
| Comp. Ex. 6 | Comp. Ex. 6 | zinc 9306 | 87.3 | 5.0 | Trace Amount | — |
| Example 64 | Example 60 | iron 19 | >99 | 3.0 | 98.5 | 88/12 |
| Example 65 | Example 61 | iron 324 | >99 | 4.2 | 93.7 | 93/7 |
| Comp. Ex. 7 | Comp. Ex. 5 | iron 3204 | 27.7 | 5.0 | Trace Amount | — |

Changes in Reaction Conditions and Catalyst Recyclability

Example 66

A 100 mL stainless steel-made autoclave equipped with a stirrer was charged with 9.0 g of trans-1,4-dicyanocyclohexane (purity 99.4%, trans isomer/cis isomer ratio=96/4, tin content 1 ppm or less) obtained in the same manner as in Example 42, 0.09 g of a catalyst (manganese-containing Raney cobalt manufactured by Kawaken Fine Chemicals Co., Ltd.), 9.6 mL of a 25 wt % ammonia water, and 11.3 g of 1-butanol. The autoclave was purged with nitrogen introduced from the autoclave nozzle inlet three times at 5 MPa, and the mixture was heated to 120° C. while stifling at 400 rpm.

When the temperature reached 120° C., hydrogen supply was started continuously to achieve a pressure of 3.5 MPa, and the reaction was performed under constant pressure until there is no hydrogen absorption. The reaction time was 3.3 hours.

After the completion of reaction, the mixture was cooled to room temperature and allowed to stand. The supernatant liquid of the reaction mixture was taken out.

The obtained liquid was analyzed by gas chromatography, and it was found that the conversion of 1,4-dicyanocyclohexane was 99.9% or more, the yield of 1,4-bis(aminomethyl)cyclohexane was 96.7%, and the trans isomer/cis isomer ratio was 91/9.

Examples 67 to 75

The catalyst remained in the autoclave after taking out the supernatant liquid in Example 66 was used as is, recovered, and reaction was performed repeatedly under the same reaction conditions as those of Example 66, using new trans-1,4-dicyanocyclohexane, ammonia water, and 1-butanol. The results are shown in Table 9. In Example 72, 0.09 g of a catalyst (manganese-containing Raney cobalt manufactured by Kawaken Fine Chemicals Co., Ltd.) was added.

The reaction was repeated 20 times, and trans-1,4-bis(aminomethyl)cyclohexane was obtained with a high yield.

TABLE 9

| | | Reaction | 1,4-dicyano- | 1,4-bis(aminomethyl)cyclohexane | |
|---|---|---|---|---|---|
| Example No. | catalyst used | Time (hr) | cyclohexane Conversion (%) | Yield (%) | trans isomer/cis isomer ratio |
| Example 66 | Manganese-containing Raney cobalt | 3.3 | >99 | 96.7 | 91/9 |
| Example 67 | Catalyst Recovered in Example 66 | 4.2 | >99 | 94.7 | 91/9 |
| Example 68 | Catalyst Recovered in Example 67 | 4.8 | >99 | 95.8 | 91/9 |
| Example 69 | Catalyst Recovered in Example 68 | 5.3 | >99 | 94.3 | 90/10 |
| Example 70 | Catalyst Recovered in Example 69 | 5.8 | >99 | 95.6 | 90/10 |
| Example 71 | Catalyst Recovered in Example 70 | 6.5 | >99 | 98.0 | 90/10 |
| Example 72 | Catalyst Recovered in Example 71 | 2.5 | >99 | 95.6 | 92/8 |
| Example 73 | Catalyst Recovered in Example 72 | 2.8 | >99 | 93.4 | 92/8 |
| Example 74 | Catalyst Recovered in Example 73 | 3.0 | >99 | 97.8 | 92/8 |
| Example 75 | Catalyst Recovered in Example 74 | 3.3 | >99 | 96.9 | 91/9 |

Isolation of High Trans Isomer Product

Example 87

A four-neck flask equipped with a stirrer, a gas inlet tube, a thermometer, a gas purge line, and a condenser was charged with 286.6 g of commercially available 1,4-cyclohexanedicarboxylic acid, 55.7 g of N,N'-dimethylimidazolidinone, and 3.6 g of tin (II) oxide. Ammonia gas and nitrogen were mixedly introduced thereto while stirring at a rate of 90 mL/min (0.14 mol equivalent/1,4-cyclohexanedicarboxylic acid/hr) and 10 mL/min, respectively. The temperature was increased to 280° C., and while the temperature was kept constant, reaction was performed. After 48 hours, the reaction mixture was cooled to 90° C.

520 g of 1-butanol was added to the mixture and stirred. The mixture was filtered by hot filtration to remove the catalyst. The filtrate was analyzed by gas chromatography, and it was found that the yield of 1,4-dicyanocyclohexane was 86%.

Next, as the filtrate obtained as described above was cooled while stirring to room temperature, a precipitate was appeared. The suspension was filtered, and 230 g of 1-butanol was added to the residue taken out. The mixture was stirred for 1 hour at 90° C., and thereafter, as the reaction mixture was cooled while stirring to room temperature, a precipitate was appeared again. The suspension was filtered, and washed twice with 1-butanol. Thereafter, the residue was dried, thereby producing 100 g of white solid (yield 45%).

The obtained white solid was analyzed by gas chromatography, and it was found that the solid was 1,4-dicyanocyclohexane having a purity of 99.5% or more, and the trans isomer/cis isomer ratio was 99/1.

Example 88

A 0.5 L stainless steel-made autoclave equipped with a stirrer was charged with 55 g of 1,4-dicyanocyclohexane having a trans isomer/cis isomer ratio of 99/1 obtained in Example 87, 3.0 g of a catalyst (Raney nickel manufactured by Kawaken Fine Chemicals Co., Ltd.), 56 mL of a 28 wt % ammonia water, and 105 mL of 1-butanol. The autoclave was purged with nitrogen introduced from the autoclave nozzle inlet three times at 5 MPa, and the mixture was heated to 80° C. while stirring at 400 rpm.

When the temperature reached 80° C., hydrogen supply was started to achieve a pressure of 4.5 MPa, and the reaction was performed until there is no hydrogen absorption. The reaction time was 3 hours.

After the completion of reaction, the mixture was cooled to room temperature. The reaction mixture was taken out, and was filtered to remove the catalyst.

The filtrate was analyzed by gas chromatography, and it was found that the conversion of 1,4-dicyanocyclohexane was 100%, the yield of 1,4-bis(aminomethyl)cyclohexane was 98%, and the trans isomer/cis isomer ratio was 98/2.

The reaction mixture was distilled under a reduced pressure of 10 mmHg, and 1,4-bis(aminomethyl)cyclohexane having a purity of 99.5% or more and a trans isomer/cis isomer ratio of 98/2 was obtained with a yield of 93%.

While the illustrative embodiments of the present invention are provided in the above description, such is for illustrative purpose only and it is not to be construed restrictively. Modification and variation of the present invention that will be obvious to those skilled in the art is to be covered by the following claims.

INDUSTRIAL APPLICABILITY

The present invention allows for an industrially advantageous production of 1,4-bis(aminomethyl)cyclohexane having a high trans isomer ratio using a raw material cheaper than conventional ones: the raw material such as terephthalic acid or terephthalic acid derivative of at least one selected from the group consisting of terephthalic acid, terephthalic acid ester, and terephthalic acid amide.

The compound is used suitably for improvement in characteristics of polyamide and polyurethane.

The invention claimed is:

1. A method for producing trans-1,4-bis(aminomethyl)cyclohexane, the method comprising:

a nuclear hydrogenation step of producing a hydrogenated terephthalic acid or terephthalic acid derivative by nuclear hydrogenation of a terephthalic acid or terephthalic acid derivative, the terephthalic acid or terephthalic acid derivative being at least one selected from the group consisting of terephthalic acid, terephthalic acid ester, and terephthalic acid amide;

a cyanation step of treating the hydrogenated terephthalic acid or terephthalic acid derivative obtained in the nuclear hydrogenation step with ammonia, thereby producing 1,4-dicyanocyclohexane, and producing trans-1,4-dicyanocyclohexane from the obtained 1,4-dicyanocyclohexane wherein in the cyanation step, a separated cis-1,4-dicyanocyclohexane is treated again with ammonia in the presence of or in the absence of the hydrogenated terephthalic acid or terephthalic acid derivative; and an aminomethylation step of treating the trans-1,4-dicyanocyclohexane obtained in the cyanation step with hydrogen, thereby producing trans-1,4-bis(aminomethyl)cyclohexane, wherein metal oxide is used as a catalyst in the cyanation step, and the obtained trans-1,4-dicyanocyclohexane has a metal content of 3000 ppm or less.

2. A method for producing trans-1,4-bis(aminomethyl)cyclohexane, the method comprising:

a cyanation step of treating a hydrogenated terephthalic acid or terephthalic acid derivative with ammonia, thereby producing 1,4-dicyanocyclohexane, and producing trans-1,4-dicyanocyclohexane from the obtained 1,4-dicyanocyclohexane wherein in the cyanation step, a separated cis-1,4-dicyanocyclohexane is treated again with ammonia in the presence of or in the absence of the hydrogenated terephthalic acid or terephthalic acid derivative; and an aminomethylation step of treating the trans-1,4-dicyanocyclohexane obtained in the cyanation step with hydrogen, thereby producing trans-1,4-bis(aminomethyl)cyclohexane, wherein metal oxide is used as a catalyst in the cyanation step, and the obtained trans-1,4-dicyanocyclohexane has a metal content of 3000 ppm or less.

3. The method for producing trans-1,4-bis(aminomethyl)cyclohexane according to claim 2, wherein the hydrogenated terephthalic acid or terephthalic acid derivative is obtained by a nuclear hydrogenation step of nuclear hydrogenation of a terephthalic acid or terephthalic acid derivative, the terephthalic acid or terephthalic acid derivative being at least one selected from the group consisting of terephthalic acid, terephthalic acid ester, and terephthalic acid amide.

4. The method for producing trans-1,4-bis(aminomethyl) cyclohexane according to claim 1, wherein in the cyanation step, the cis isomer and the trans isomer in the 1,4-dicyanocyclohexane obtained by the reaction with ammonia are separated, and the separated trans-1,4-dicyanocyclohexane is used in the aminomethylation step.

5. The method for producing trans-1,4-bis(aminomethyl) cyclohexane according to claim 1, wherein in the cyanation step, trans-1,4-dicyanocyclohexane is separated from 1,4-dicyanocyclohexane by crystallization using an aqueous solvent, and in the crystallization step of the cyanation step and in the aminomethylation step, the same aqueous solvent is used.

6. The method for producing trans-1,4-bis(aminomethyl) cyclohexane according to claim 1, wherein in the cyanation step, the reaction with ammonia is performed while heating to 200 to 350° C.

7. The method for producing trans-1,4-bis(aminomethyl) cyclohexane according to claim 1, wherein in the cyanation step, the reaction with ammonia is performed in the presence of a solvent having a boiling point of 180° C. to 350° C.

8. The method for producing trans-1,4-bis(aminomethyl) cyclohexane according to claim 1, wherein in the cyanation step, the reaction with ammonia is performed in the presence of 3 to 20 parts by weight of a solvent relative to 100 parts by weight of the hydrogenated terephthalic acid or terephthalic acid derivative.

9. The method for producing trans-1,4-bis(aminomethyl) cyclohexane according to claim 1, wherein a solvent is used in the cyanation step, the solvent being selected from o-dichlorobenzene, triethylene glycol dimethylether, tetraethylene glycol dimethylether, N-methyl-2-pyrrolidinone, N,N'-dimethylimidazolidinone, N,N'-diethylimidazolidinone, N,N'-dipropylimidazolidinone, N,N',4-trimethylimidazolidinone, and N,N'-dimethylpropyleneurea.

10. The method for producing trans-1,4-bis(aminomethyl) cyclohexane according to claim 1, wherein in the cyanation step, the ammonia to be brought into contact with is fed at a rate greater than 0.5 mol equivalent/hydrogenated terephthalic acid or terephthalic acid derivative/hr.

11. The method for producing trans-1,4-bis(aminomethyl) cyclohexane according to claim 2, wherein in the cyanation step, the cis isomer and the trans isomer in the 1,4-dicyanocyclohexane obtained by the reaction with ammonia are separated, and the separated trans-1,4-dicyanocyclohexane is used in the aminomethylation step.

12. The method for producing trans-1,4-bis(aminomethyl) cyclohexane according to claim 2, wherein in the cyanation step, trans-1,4-dicyanocyclohexane is separated from 1,4-dicyanocyclohexane by crystallization using an aqueous solvent, and in the crystallization step of the cyanation step and in the aminomethylation step, the same aqueous solvent is used.

13. The method for producing trans-1,4-bis(aminomethyl) cyclohexane according to claim 2, wherein in the cyanation step, the reaction with ammonia is performed while heating to 200 to 350° C.

14. The method for producing trans-1,4-bis(aminomethyl) cyclohexane according to claim 2, wherein in the cyanation step, the reaction with ammonia is performed in the presence of a solvent having a boiling point of 180° C. to 350° C.

15. The method for producing trans-1,4-bis(aminomethyl) cyclohexane according to claim 2, wherein in the cyanation step, the reaction with ammonia is performed in the presence of 3 to 20 parts by weight of a solvent relative to 100 parts by weight of the hydrogenated terephthalic acid or terephthalic acid derivative.

16. The method for producing trans-1,4-bis(aminomethyl) cyclohexane according to claim 2, wherein a solvent is used in the cyanation step, the solvent being selected from o-dichlorobenzene, triethylene glycol dimethylether, tetraethylene glycol dimethylether, N-methyl-2-pyrrolidinone, N,N'-dimethylimidazolidinone, N,N'-diethylimidazolidinone, N,N'-dipropylimidazolidinone, N,N',4-trimethylimidazolidinone, and N,N'-dimethylpropyleneurea.

17. The method for producing trans-1,4-bis(aminomethyl) cyclohexane according to claim 2, wherein in the cyanation step, the ammonia to be brought into contact with is fed at a rate greater than 0.5 mol equivalent/hydrogenated terephthalic acid or terephthalic acid derivative/hr.

* * * * *

UNITED STATES PATENT AND TRADEMARK OFFICE

CERTIFICATE OF CORRECTION

PATENT NO. : 8,865,939 B2
APPLICATION NO. : 13/878090
DATED : October 21, 2014
INVENTOR(S) : Naritoshi Yoshimura et al.

It is certified that error appears in the above-identified patent and that said Letters Patent is hereby corrected as shown below:

In the Specification

In column 12, line 27 should read:

preferably 0.5 to 5MPa.

Signed and Sealed this
Seventeenth Day of March, 2015

Michelle K. Lee
*Director of the United States Patent and Trademark Office*